(12) United States Patent
Atala et al.

(10) Patent No.: US 9,056,093 B2
(45) Date of Patent: Jun. 16, 2015

(54) REGENERATION OF PANCREATIC ISLETS BY AMNIOTIC FLUID STEM CELL THERAPY

(75) Inventors: Anthony Atala, Winston-Salem, NC (US); Anna Milanesi, Winston-Salem, NC (US); Shay Soker, Greensboro, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 1087 days.

(21) Appl. No.: 11/327,074

(22) Filed: Jan. 6, 2006

(65) Prior Publication Data

US 2007/0031384 A1 Feb. 8, 2007

Related U.S. Application Data

(60) Provisional application No. 60/642,381, filed on Jan. 7, 2005.

(51) Int. Cl.
| | | |
|---|---|---|
| A61K 38/00 | (2006.01) |
| A61K 35/12 | (2006.01) |
| A61K 35/39 | (2015.01) |
| A61K 9/00 | (2006.01) |
| A61K 35/50 | (2015.01) |
| A61K 38/17 | (2006.01) |
| C12N 5/073 | (2010.01) |
| C12N 5/074 | (2010.01) |
| C12N 5/071 | (2010.01) |

(52) U.S. Cl.
CPC ............... *A61K 35/39* (2013.01); *A61K 38/00* (2013.01); *A61K 9/0019* (2013.01); *A61K 35/12* (2013.01); *A61K 35/50* (2013.01); *A61K 38/1709* (2013.01); *C12N 5/0605* (2013.01); *C12N 5/0607* (2013.01); *C12N 5/0676* (2013.01); *C12N 2501/60* (2013.01); *C12N 2506/02* (2013.01); *C12N 2506/03* (2013.01); *C12N 2510/00* (2013.01)

(58) Field of Classification Search
CPC ............................... A61K 38/00; A61K 35/12
USPC ................................................. 435/325, 366
See application file for complete search history.

(56) References Cited

U.S. PATENT DOCUMENTS

| | | | |
|---|---|---|---|
| 2,819,199 A * | 1/1958 | Kalish ........................... 514/23 |
| 6,703,017 B1 | 3/2004 | Peck et al. |
| 6,774,120 B1 | 8/2004 | Ferber |
| 6,815,203 B1 | 11/2004 | Bonner-Weir et al. |
| 7,033,831 B2 * | 4/2006 | Fisk et al. ...................... 435/377 |
| 7,569,385 B2 | 8/2009 | Haas |
| 2002/0164307 A1 | 11/2002 | Habener et al. |
| 2002/0182728 A1 | 12/2002 | Ramiya et al. |
| 2003/0003088 A1 | 1/2003 | Tsao et al. |
| 2003/0083497 A1 * | 5/2003 | Bouchard et al. ............. 544/405 |
| 2003/0180269 A1 | 9/2003 | Hariri |
| 2003/0235563 A1 * | 12/2003 | Strom et al. ................ 424/93.21 |
| 2005/0054102 A1 | 3/2005 | Wobus et al. |
| 2005/0118712 A1 | 6/2005 | Tsai et al. |
| 2006/0160218 A1 | 7/2006 | Slack et al. |
| 2006/0216277 A1 * | 9/2006 | Efrat ........................... 424/93.21 |

FOREIGN PATENT DOCUMENTS

| | | |
|---|---|---|
| WO | WO 02/36751 A1 | 5/2002 |
| WO | WO 02/36751 A2 | 5/2002 |
| WO | WO 03/026584 A2 | 4/2003 |
| WO | WO 03-042405 A2 | 5/2003 |
| WO | WO 03/047607 A1 | 6/2003 |

OTHER PUBLICATIONS

Limbert et al., Beta-cell replacement and regeneration: Strategies of cell-based therapy for type 1 diabetes mellitus. Diabetes Res Clin Pract. 79(3):389-99, 2008.*
Ren et al., Pancreatic islet cell therapy for type I diabetes: understanding the effects of glucose stimulation on islets in order to produce better islets for transplantation. J Transl Med. Jan. 3, 2007; 5:1-15.*
Wilding et al., The role of pdx1 and HNF6 in proliferation and differentiation of endocrine precursors. Diabetes Metab Res Rev. 20(2): 114-23, 2004.*
Lyttle et al., Transcription factor expression in the developing human fetal endocrine pancreas, Diabetologia 51(7):1169-80, 2008.*
Tsai et al. (2004, Human Reproduction, vol. 19(6), pp. 1450-1456).*
Spangrude et al. (1993, Blood, vol. 82, pp. 3327-3332).*
International Search Report and Written Opinion, PCT/US06/00334, date of mailing Jun. 23, 2008.
De Coppi P et al. Isolation of amniotic stem cell lines with potential for therapy. Nature Biotechnology. Jan. 2007;25(1):100-106.
Ferber S et al. Pancreatic and duodenal homeobox gene 1 induces expression of insulin genes in liver and ameliorates streptozotocin-induced hyperglycemia. Nature Medicine. May 2000; 6(5):568-572.
Ber I et al. Functional, persistent, and extended liver to pancreas transdifferentiation. The Journal of Biological Chemistry. Aug. 200, 2003; 278(34): 31950-31957.
Sapir T et al. Cell-replacement therapy for diabetes: generating functional insulin-producing tissue from adult human liver cells. PNAS. May 31, 2005; 102(22): 7964-7969.
Miki T et al. Stem cell characteristics of amniotic epithelial cells. Stem Cells. 2005; 23: 1549-1559.

(Continued)

*Primary Examiner* — Anoop Singh
*Assistant Examiner* — David A Montanari
(74) *Attorney, Agent, or Firm* — Myers Bigel Sibley & Sajovec, P.A.

(57) ABSTRACT

A method of treating diabetes in a mammalian subject is carried out by: (a) providing mammalian amniotic fluid stem cells, and then (b) administering the cells to the subject in an amount effective to treat diabetes. Optionally, the cells may be differentiated into pancreatic-like cells or at least treated to initiate subsequent differentiation into-pancreatic-like cells, prior to administration.

32 Claims, 14 Drawing Sheets

(56) References Cited

OTHER PUBLICATIONS

Mitchell DA and Nair SK. RNA-transfected dendritic cells in cancer immunotherapy. J. Clin. Invest. Nov. 1, 2000; 106(9): 1065-1069.
Invitrogen Corporation. pcDNA™3.1(+); pcONA™3.1(−): catalog Nos. V790-20 and V795-20, respectively. User Manual Version J. (Aug. 5, 2008) 22 pp. Invitrogen Corporation, Carlsbad, CA.
Examination Report, EP 06717519, mailed Jul. 12, 2013.
Lyttle et al., *Transcription factor expression in the developing human fetal endocrine pancreas* Diabetologia 51:1169 (2008).
McKinnon et al., *Pancreatic duodenal homeobox-1, Pdx-1, a major regulator of beta cell identity and function*, Diabetologia 44(10):1203 (2001).
McLin et al., *Organogenesis: Making pancreas from liver*, Current Biol. 13(3):R96 (2003).
Ramiya et al., *Reversal of insulin-dependent diabetes using islets generated in vitro from pancreatic stem cells* Nature Medicine 6(3):278 (2000).
Tamagawa et al., *Establishment and characterization of a pluripotent stem cell line derived from human amniotic membranes and initiation of germ layers in vitro* Human Cell 17(3):125 (2004).
Tang et al., *In vivo and in vitro characterization of insulin-producing cells obtained from murine bone marrow*, Diabetes 53:1721 (2004).
Thomson Scientific, AN 2003-493589 ; XP-002574798, WPI Database Week 46 (2003).
Examination Report, CA 2593549, mailed Jun. 10, 2013.
Ramiya VK et al. Reversal of insulin-dependent diabetes using islets generated in vitro from pancreatic stem cells. Nature Medicine. Mar. 2000; 6(3): 278-282.
Nikaido T. Database WPI Week 200346. AN 2003-493589 & WO 03/047607 A1 Jun. 12, 2003. 2 pp. Thomson Scientific, London, GB.
Tamagawa T et al. Establishment and characterization of a pluripotent stem cell line derived from human amniotic membranes and initiation of germ layers in vitro. Human Cell. 2004; 17(3): 125-130.
Lyttle BM et al. Transcription factor expression in the developing human fetal endocrine pancreas. Diabetologia. 2008; 51: 1169-1180.
Supplementary European Search Report, EP 06717519, mailed Apr. 19, 2010.

* cited by examiner

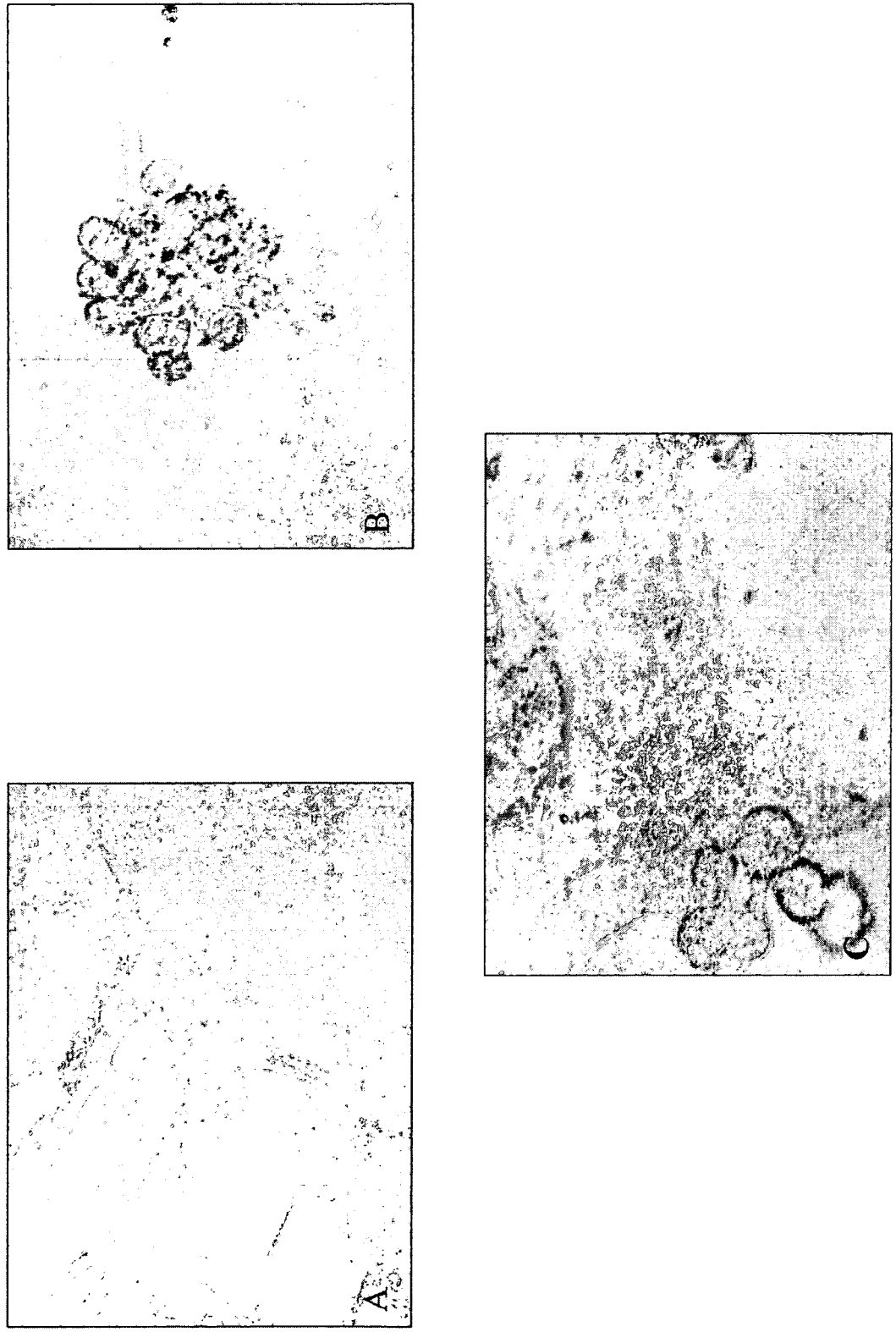
Fig 1. Morphological changes of mAFSC after adenovirus-Pdx1 infection in vitro.

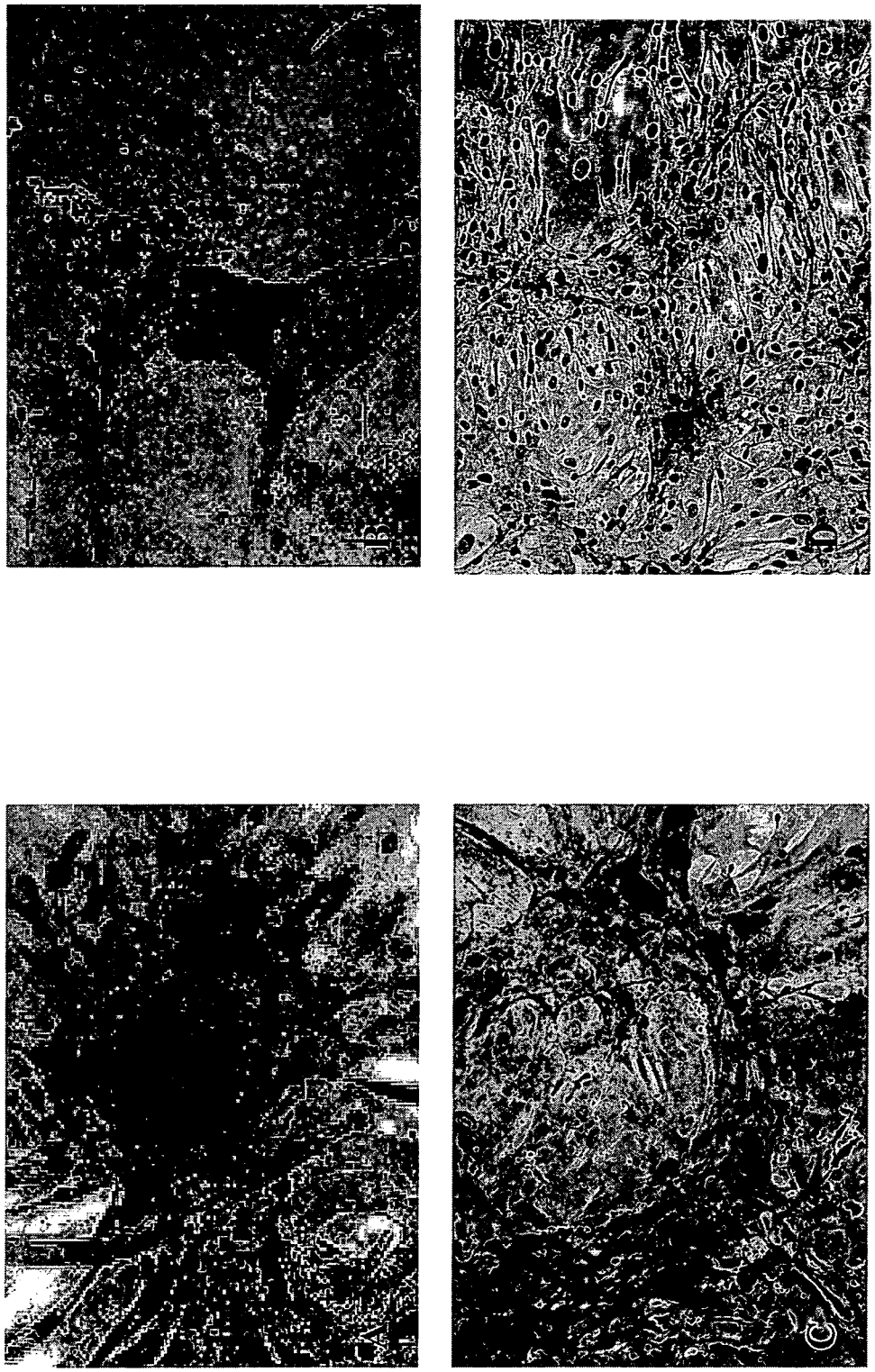
Fig 2. In vitro mAFSC express pancreatic islet markers after 20 days from adenovirus-Pdx1 infection.

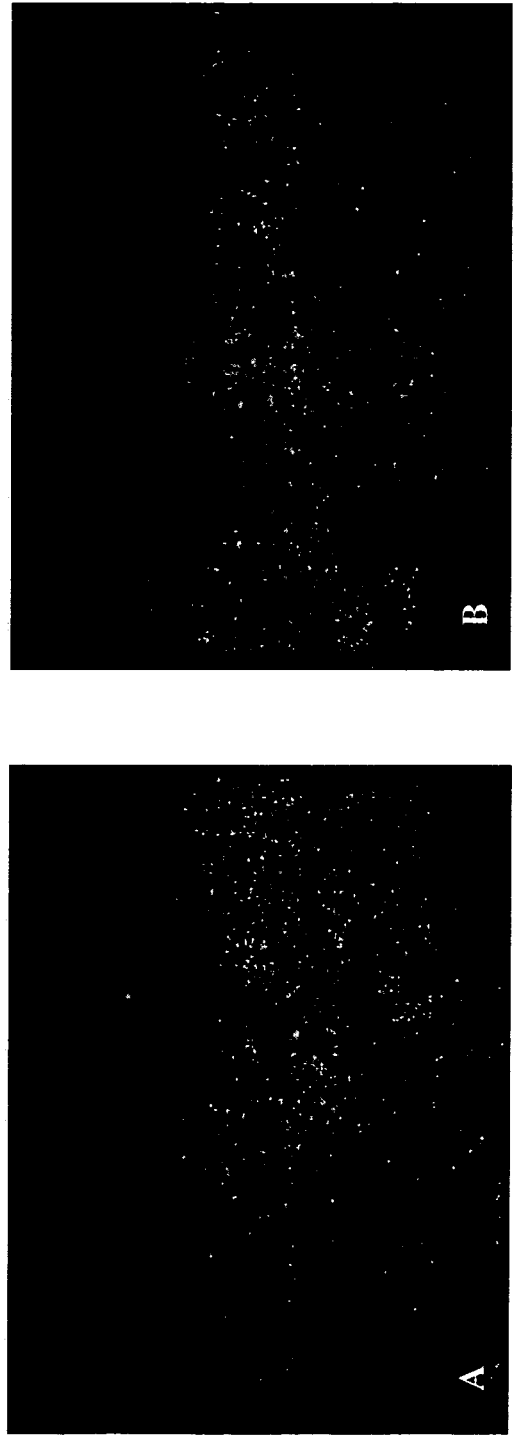
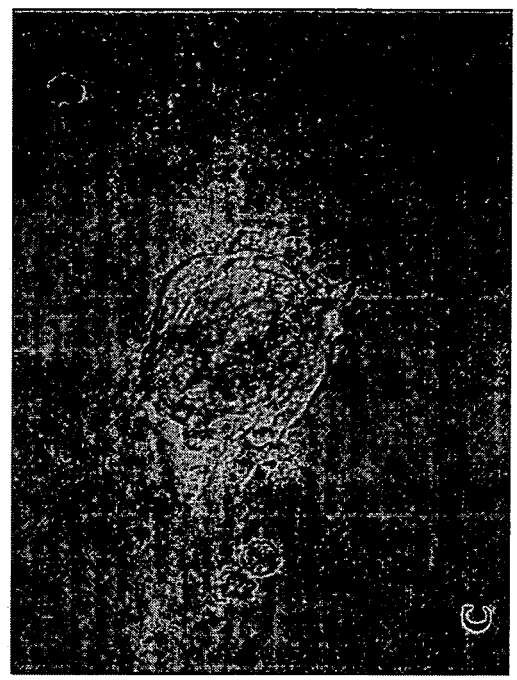
Fig 3. Expression of insulin and glucagon in the pancreatic islets-like structures after adenovirus-Pdx1 infection.

Fig 4. Expression of Pdx1, Pax6 andNgn3 after adenovirus-Pdx1 infection
Fig 4.A Western Blot
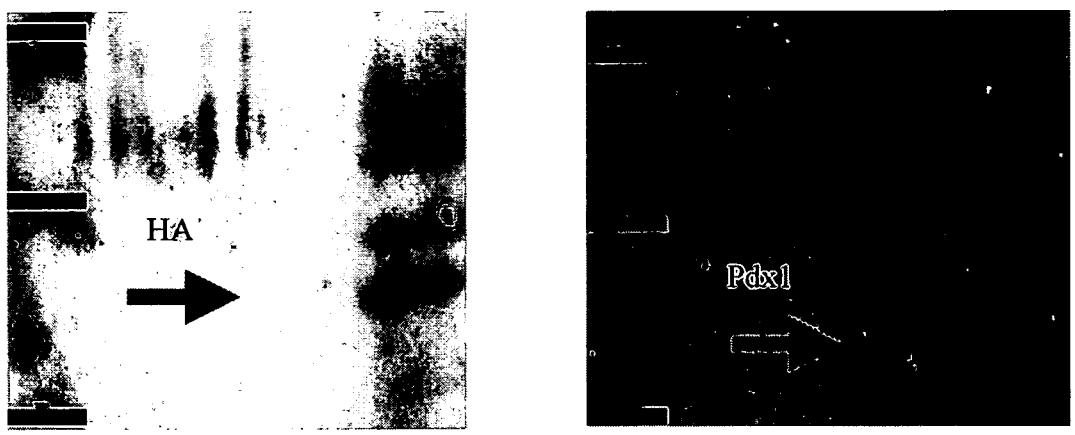
Fig 4.B  RT-PCR
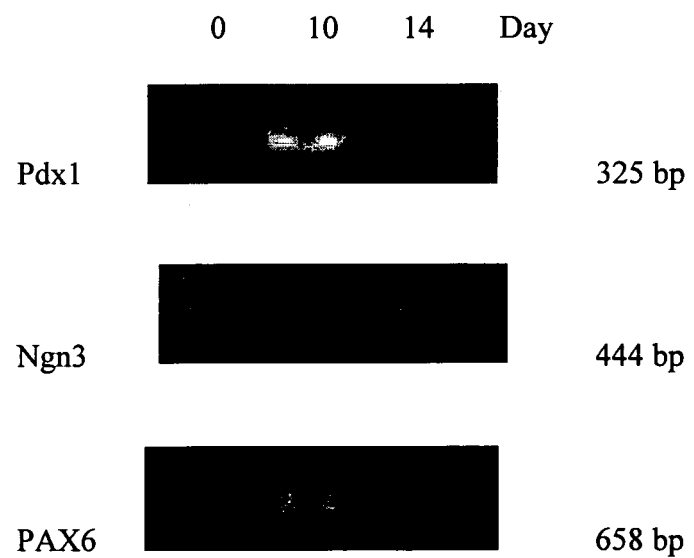

Fig 5. Induction of hyperglycemia after streptozotocine (STZ) treatment in NOD/SCID mice.
Fig 5.A
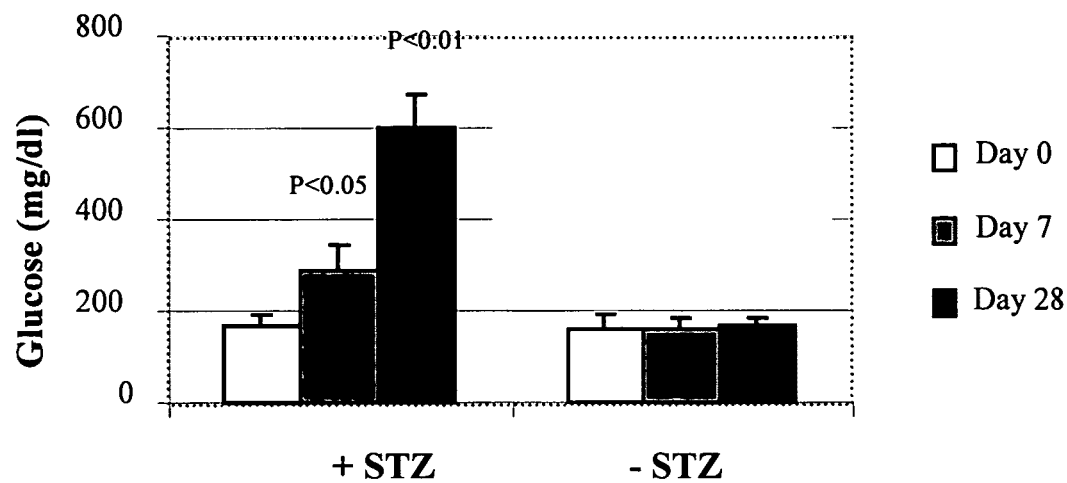
Fig 5.B
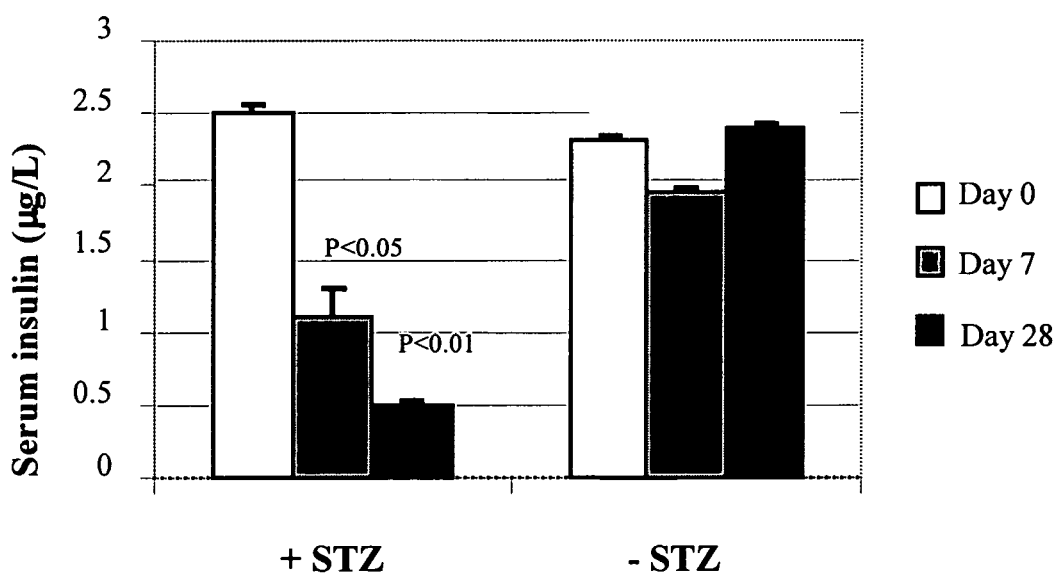

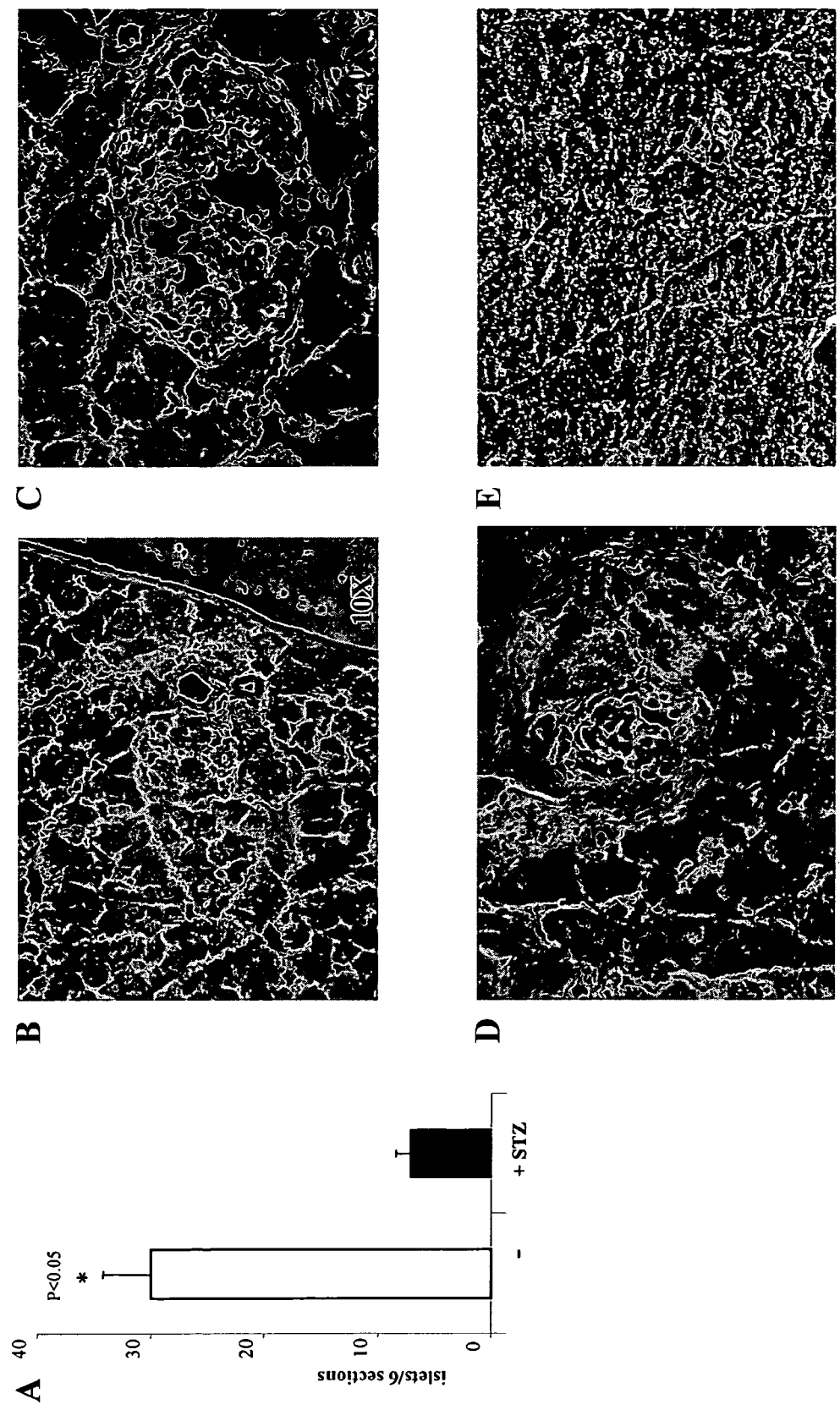
Fig 6. Number and morphology of pancreatic islets after STZ-treatment.

Fig 7. Prevention of increasing and reduction of blood glucose in onset diabetic mice after transplantation of mAFSC.

Fig 8. Reduction of blood glucose correlated with increasing of systemic insulin and maintaining of body weight.

Fig 9. Maintaining of euglycemia in STZ-treated mice transplanted with mAFSC(Ad-Pdx1).
Fig 9A
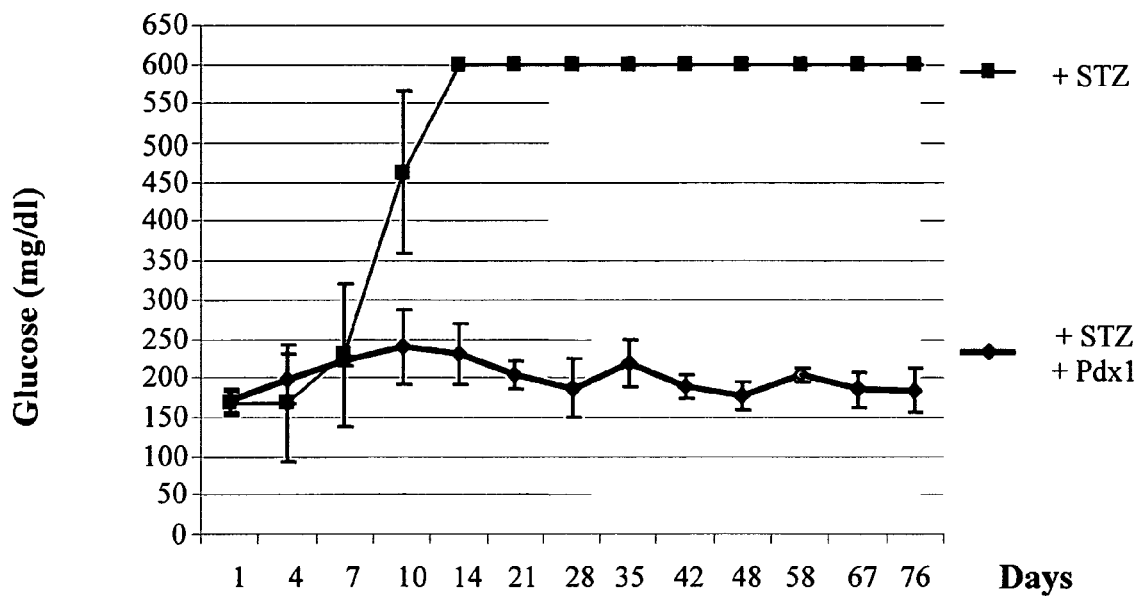
Fig 9B. Glucose tolerance test.
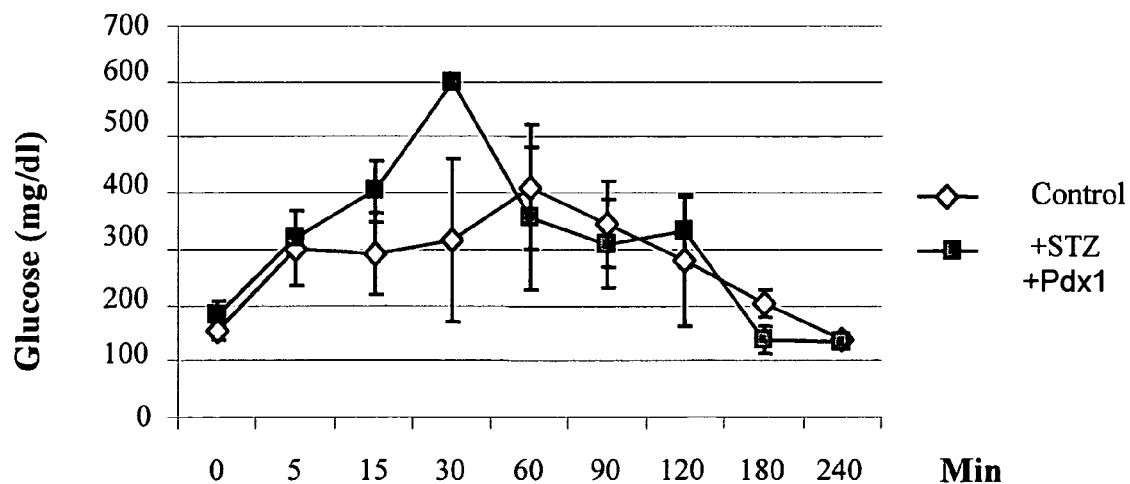

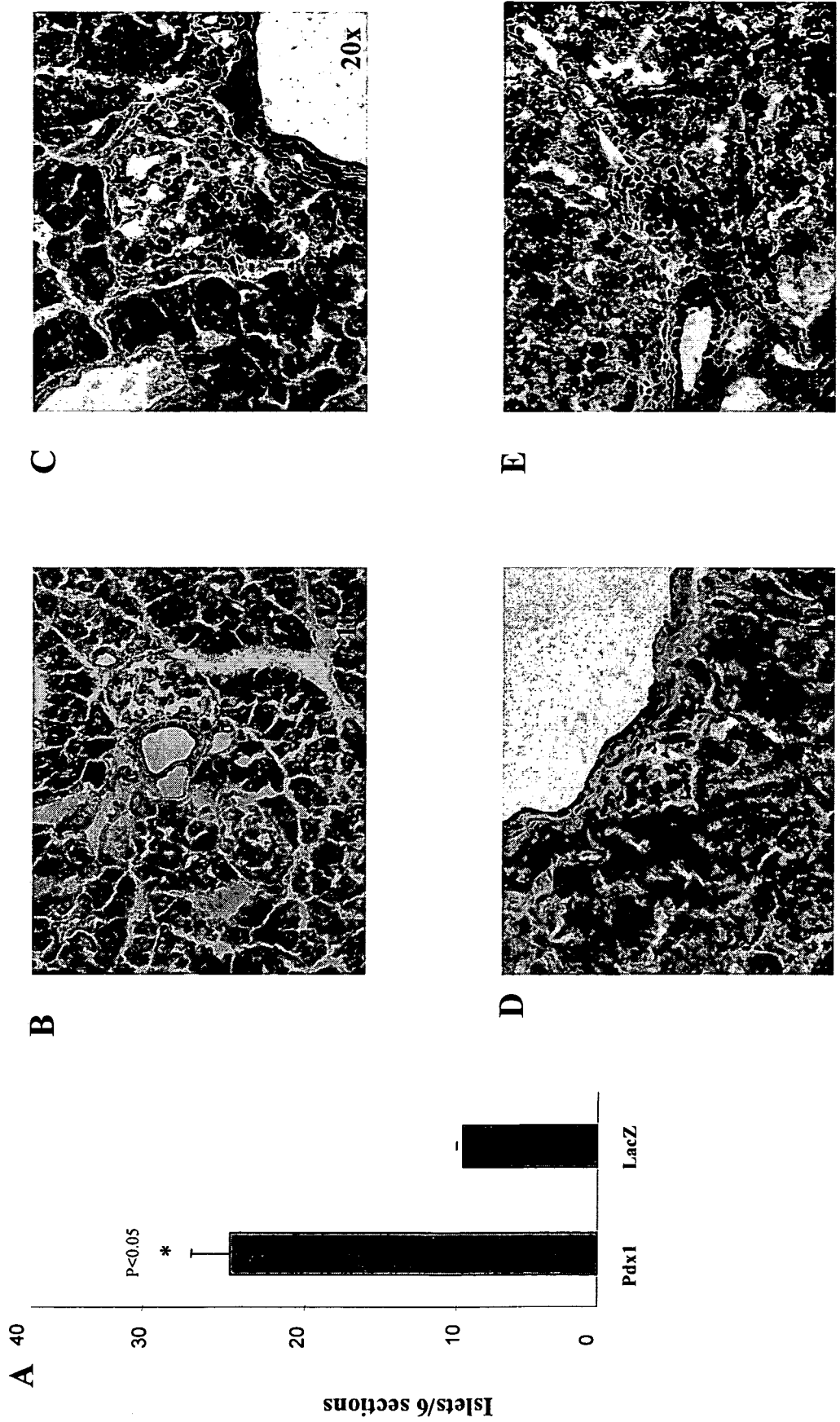
Fig 10. Number and morphology of pancreatic islets after mAFSC transplantation.

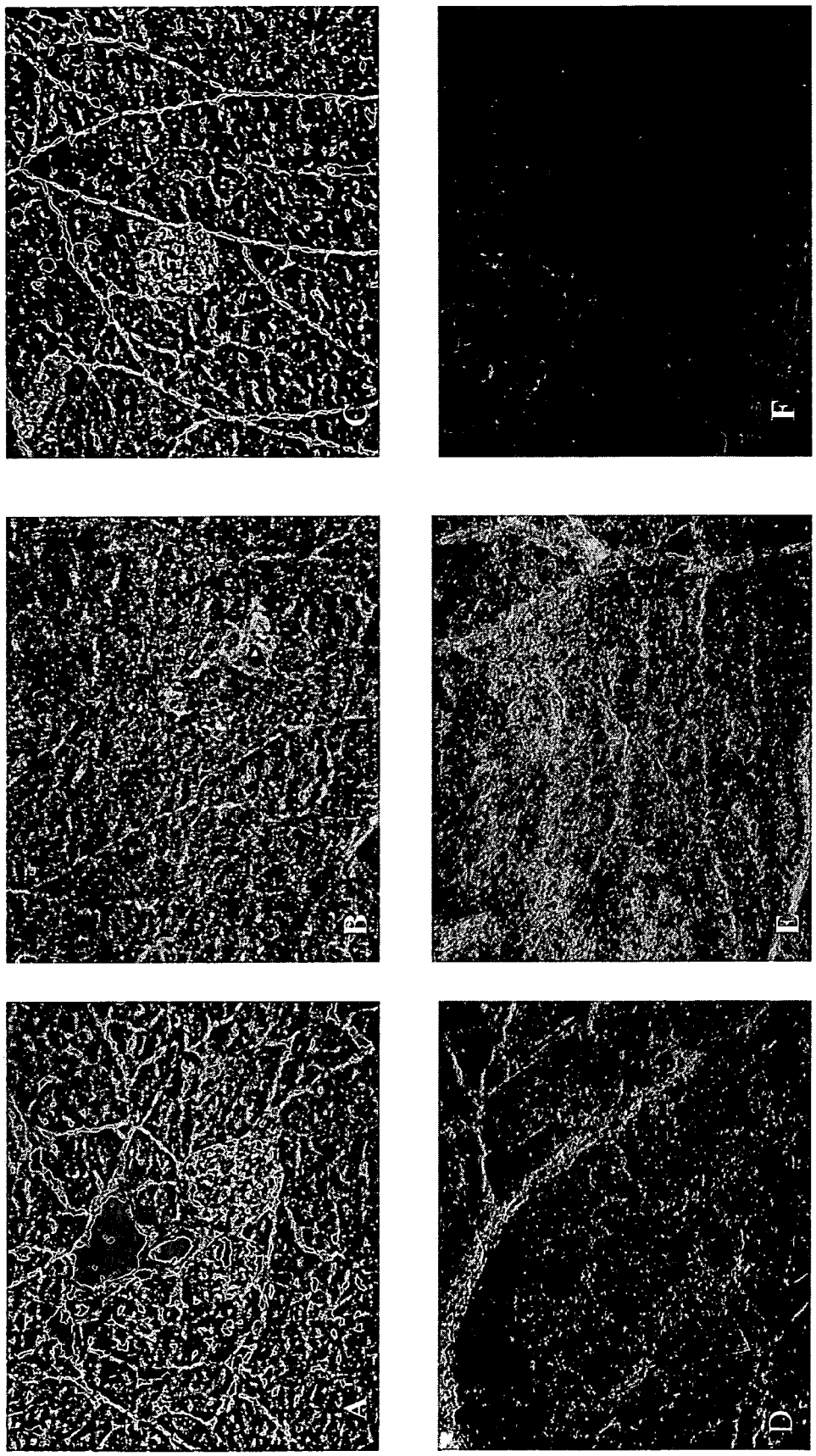
Fig 11. H&E and insulin staining after mAFSC transplantation.

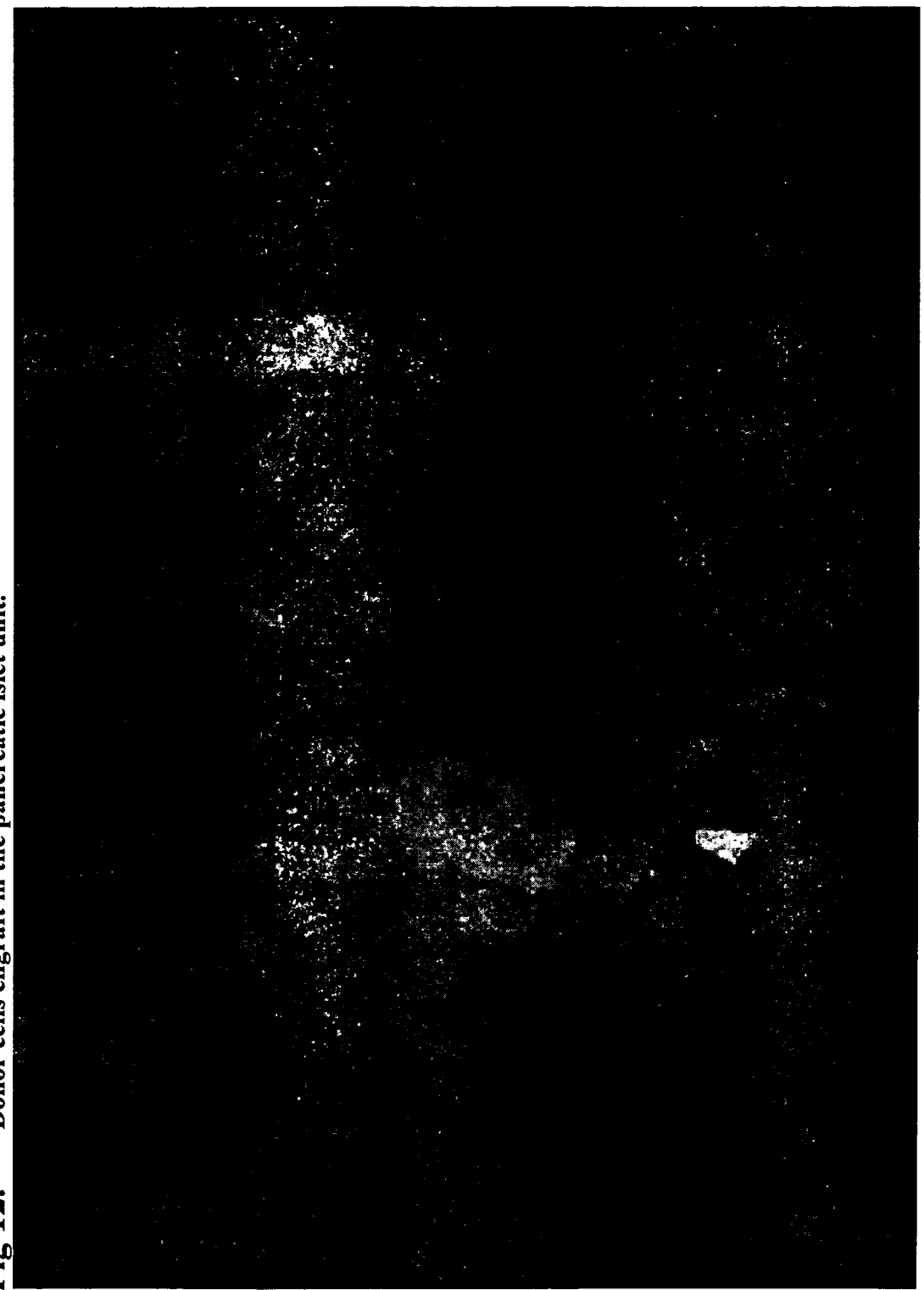
Fig 12. Donor cells engraft in the pancreatic islet unit.

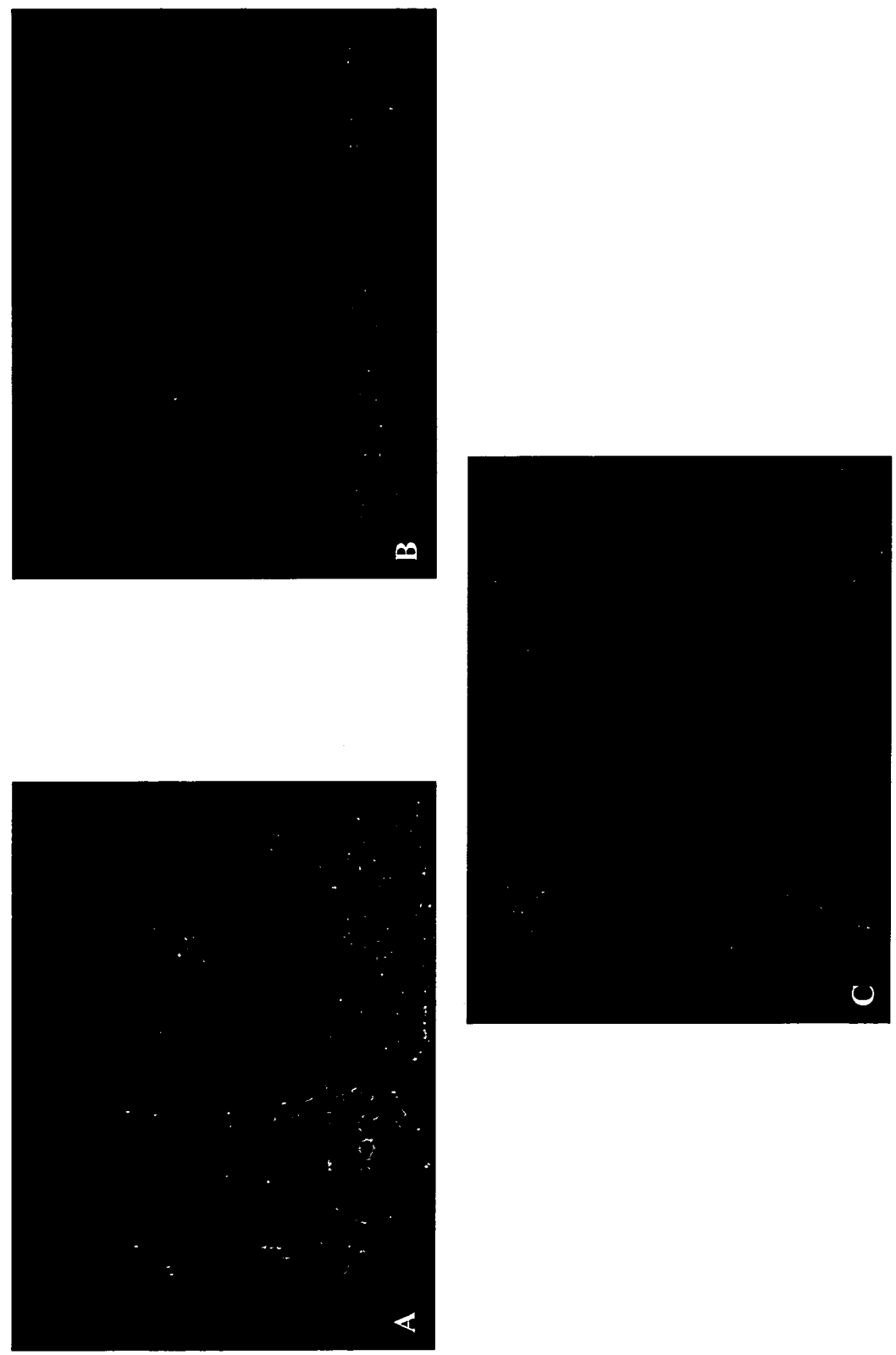
Fig 13. Donor cells in the pancreatic islet unit express insulin.

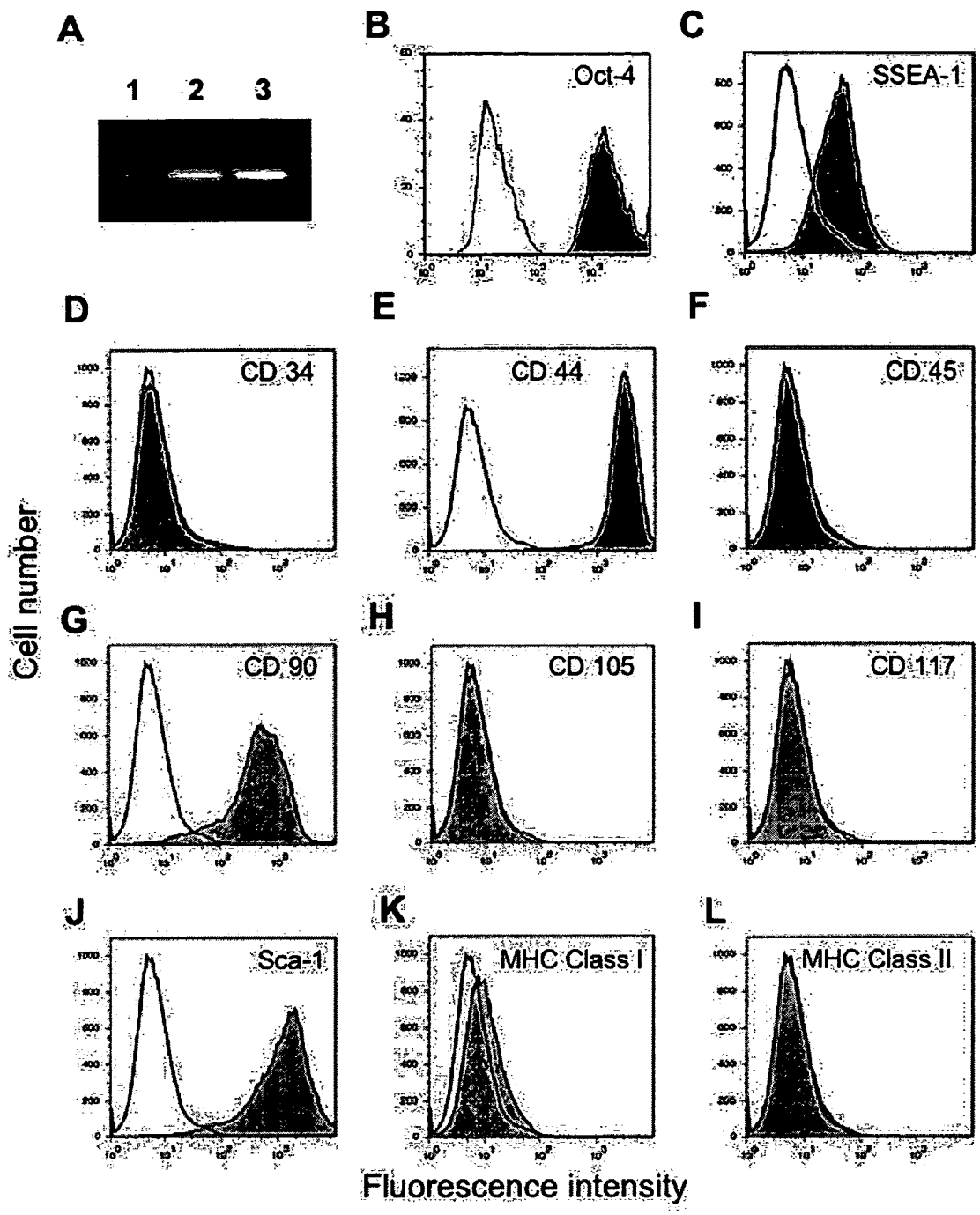
Figure 14. Marker expression

REGENERATION OF PANCREATIC ISLETS BY AMNIOTIC FLUID STEM CELL THERAPY

RELATED APPLICATIONS

This application claims the benefit of U.S. Provisional Patent Application Ser. No. 60/642,381, filed Jan. 7, 2005, the disclosure of which is incorporated by reference herein in its entirety.

FIELD OF THE INVENTION

The present invention concerns methods and composition for the treatment of diabetes in subjects in need of such treatment.

BACKGROUND OF THE INVENTION

The glucose concentration in the bloodstream of healthy organisms is tightly regulated via hormones of the pancreas, especially insulin. Insulin is produced by endocrine pancreatic β-cells, the major component of the islets of Langerhans. Lack of or a defect in insulin-producing cells produces diabetes, a devastating disease suffered by 150 million people world-wide (prevalence 4.6% in the range of 20-79 years).

Following the discovery of insulin in 1921 by Banting and Best, insulin therapy has saved the lives of many type 1 and type 2 diabetes mellitus patients. However, 50% of diabetics develop chronic diabetes-related complications that appear years after the onset of diabetes (including blindness, renal failure, myocardial infarction, and non-traumatic amputation) [Ritz, E. and Schomig M., *The diabetic patient with renal failure*. Nefrologia, 2000. 20: p.16-24; Brownlee M., *Biochemistry and molecular cell biology of diabetic complications*. Nature, 2001. 414: p. 813-820].

Several clinical trials have demonstrated that strict glycemic control can slow and even prevent the progression of diabetes complications. However, intensive insulin therapy increases the incidence of hypoglycemic episodes. In recent years, allotransplantation has been extensively investigated as a potential treatment for diabetes mellitus type 1. However, follow up studies indicate that most of the recipients continue to exhibit abnormal blood glucose control [Paty, B. W., et al., *Intrahepatic islet transplantation in type I diabetic patients does not restore hypoglycemic hormonal counterregulation or symptom recognition after insulin independence*. Diabetes, 2002. 51(12): p. 3428-34]. In addition, these procedures require life-long suppression of the immune system and are restricted by the limited tissue supply from cadaver donors.

One of the most promising potential future therapeutic options for the treatment of diabetes is the transplantation of cells producing insulin. Transplantation of new insulin-producing cells, in the form of all pancreas or isolated cells in combination with a specific immune-suppression regime, has been shown to ameliorate the disease by eliminating the need for exogenous insulin and normalizing glycerinated hemoglobin levels [Shapiro, A. M., et al., *Islet transplantation in seven patients with type 1 diabetes mellitus using a glucocorticoid-free immuno-soppressive regimen*. N Engl J Med, 2000. 343: p. 230-238; Ricordi, C., *Islet transplantation: a brave new world*. Diabetes, 2003. 52: p. 1595-1603]. However, freshly isolated islets from at least two immunologically compatible donors are necessary for these transplantations. Because suitable donor tissue is limited and the proliferative capacity of islets cells is very low, a wide-scale application of islet transplantation for diabetic patients is difficult. Forced ex vivo expansion of human islets has resulted in premature senescence and dedifferentiation. An alternative option would be the use of xenogeneic tissue, such as porcine islets, but the need for strong immune suppression and the risk of retroviral infections create barriers for clinical application [Butler, D., *Last chance to stop and think on risks of xenotransplants*. Nature, 1998. 391: p. 320-324].

Hence, the generation of insulin secreting β-cells by genetic engineering or by the differentiation of stem cells has become a major goal of diabetic research. The generation of β-cell lines has been attempted using both β-cell and non-β-cell materials. The generation of immortalized human β-cell lines has been more challenging because human β-cells are difficult to propagate and tend to lose their differentiated function. Limited β-cell differentiation has been achieved in βlox5 cells, a cell line derived from purified adult β-cells [Itkin-Ansary, P., et al., *Cell-based therapies for diabetes: progress towards a transplantable human β-cell line*. Ann NY Acad Sci, 2003. 1005: p. 138-147]. However, the induction of differentiation was complex, variable, and βlox5 cells exhibited a tendency to lose insulin expression over time. The engineering of insulin-producing cells from somatic cells has also so far failed.

Another promising alternative for the regeneration of pancreatic islets might be stem cells located in embryonic and adult tissue. Stem cell researchers are investigating how both pluripotent embryonic stem cell and multipotent adult stem cell populations might be used to develop cell therapy strategies. Indeed, recent results with pluripotent cells from pancreas, bone marrow, and embryo open interesting possibilities for future therapy. [Zulewski, H., et al., *Multipotential nestin-positive stem cells isolated from adult pancreatic islets differentiate ex vivo into pancreatic endocrine, exocrine, and hepatic phenotypes*. Diabetes, 2001. 50(3): p. 521-33; Bonner-Weir, S., et al., *In vitro cultuvation of human islets from expanding ductal tissue*. Proc Natl Acad Sci USA, 2000. 97: p. 7999-80004; Ianus, A., et al., *In vivo derivation of glucose-competent pancreatic endocrine cells from bone marrow without evidence of cell fusion*. J Clin Invest, 2003. 111(6): p. 843-50; Oh, S H., et al., *Adult bone marrow-derived stem cells trans-differentiate into insulin-producing cells for the treatment of type 1 diabetes*. Lab inv, 2004. 84: p. 607-617; Soria, B., et al., *Insulin-secreting cells derived from embryonic stem cells normalize glycemia in streptozotocin-induced diabetic mice*. Diabetes, 2000. 49(2): p. 157-62; Assady, S., et al., *Insulin production by human embryonic stem cells*. Diabetes, 2001. 50(8): p. 1691-7; Blyszczuk, P., et al., *Expression of Pax4 in embryonic stem cells promotes differentiation of nestin-positive progenitor and insulin-producing cells*. Proc Natl Acad Sci U S A, 2003. 100(3): p. 998-1003; Hori, Y., et al., *Growth inhibitors promote differentiation of insulin-producing tissue from embryonic stem cells*. Proc Natl Acad Sci U S A, 2002. 99(25): p. 16105-10]

Pancreatic stem cells residing within duct epithelium have been used to generated mouse and human islets-like clusters that partially reverse insulin-dependent diabetes in an animal model [Ramiya, V. K., et al., *Reversal of insulin-dependent diabetes using islets generated in vitro from pancreatic stem cells*. Nat Med, 2000. 6(3): p. 278-82],. However the islets-like clusters generated in vitro contained β-cells with immature phenotypes, expressed low levels of insulin, and exhibited low proliferation rates, all of which may limit its wide scale application. There is also some experimental evidence indicating that stem cell-like progenitors exist within the islet [Zulewski, H., et al., *Multipotential nestin-positive stem cells isolated from adult pancreatic islets differentiate ex vivo into pancreatic endocrine, exocrine, and hepatic phenotypes*.

Diabetes, 2001. 50(3): p. 521-33]. These cells were identified on the basis of their expression of the neuroepithelial stem cell marker, nestin. Although nestin was one of the selection markers used in generating insulin-positive cells from ES cells, the use of nestin as a markers of pancreatic epithelial progenitors remains hotly debated. Several reports have shown compelling evidence that during mouse, rat, and human pancreas embryonic development, in the adult organ or during regeneration of pancreatic tissue, islet cells arise from precursors that do not express nestin [Selander, L., *Nestin is express in mesemchymal and not epithelial cells of the developing mouse pancreas*. Mech Dev, 2002. 113: p. 189-192; Lardon, J., et al., *Nestin expression in the pancreatic stellate cells and angiogenic endothelial cells*. Histochem Cell Biol, 2002. 117: p. 535-540; Piper, K., et al., *Beta-cell differentiation during human development does not rely on nestin-positive precursors: implication for stem cell-derived replacement therapy*. Diabetologia, 2002. 45: p. 1045-1047].

Rodent liver stem cells and human fetal liver cells have been differentiated towards a pancreatic endocrine phenotype in vitro by culture methods and/or introduction of beta cell specific genes. When transplanted these cells reverse diabetes mellitus in rodents [Piper et al., supra]. Cells within liver that can differentiate into insulin-secreting cells after introduction of β-cell-specific genes have also be seen in vivo after adenovirus gene-delivery into rodents [Meivar-Levy, I. and S. Ferber, *New organs from our own tissues: liver-to-pancreas transdifferentiation*. Trends Endocrinol Metab, 2003. 14(10): p. 460-6; Kojima. H., et al., *NeuroD-betacellulin gene therapy induces islets neogenesis in the liver and reverses diabetes in mice*. Nat Med, 2003. 9: p. 596-603].

A bone-fide pancreatic stem cell for β-cell regeneration remains elusive. A genetic-marking study in mice casts doubts on the existence of any β-cell progenitors and suggests that β-cells regenerate only by proliferation of existing β-cells [Dor, Y., et al., *Adult pancreatic β-cells are formed by self-duplication rather than stem-cell differentiation*. Nature, 2004. 429: p. 41-46].

Yuehua et al recently identified a rare cell within human bone marrow mesenchymal stem cell cultures that can be expanded for more than 80 population doublings. These cells are called multipotent adult progenitor cells (MAPCs) [Jiang, Y., et al., *Pluripotency of mesenchymal stem cells derived from adult marrow*. Nature, 2002. 418: p. 41-49]. These cells differentiate in vitro to cells of the three germ layers and contribute the most somatic tissue when injected into an early blastocyst. These results indicate that MAPCs are pluripotent cells, able to differentiate in many somatic tissues. 1-2 months after bone marrow transplantation, donor derived cells are found in pancreatic islets of recipient mice [Bonner-Weir, S., et al., *In vitro cultuvation of human islets from expanding ductal tissue*. Proc Natl Acad Sci U S A, 2000. 97: p. 7999-80004], but only about 1-3% of the islets cells originated from bone marrow cells. Similar experiment in diabetic mouse [Hess, D., et al., *Bone-marrow-derived stem cells initiate pancreatic regeneration*. Nat Biot, 2003. 21: p. 763-769] showed that transplantation of adult bone marrow-derived stem cells reduced hyperglycemia by helping endogenous pancreatic regeneration. In the pancreatic tissue bone marrow cells had differentiated into endothelial cells and occasionally into insulin-producing cells. An interesting recent report describes the generation of insulin-producing cells in liver, adipose tissue, spleen and bone marrow in diabetic mice and bone marrow transplantation has shown that most if not all extra pancreatic insulin-producing cells derived from donor bone-marrow [Ianus, A., et al., *In vivo derivation of glucose-competent pancreatic endocrine cells from bone marrow without evidence of cell fusion*. J Clin Invest, 2003. 111(6): p. 843-50].

ES cells are hoped to someday provide a potentially unlimited source of cells suitable for the generation of insulin-producing cells. ES cells can also be genetically manipulated to reduce or avoid graft reaction by modification of immune response [Odorico, J. S., et al., *Multilineage differentiation from human embryonic stem cell lines*. Stem Cells, 2001. 19: p. 193-204]. Mouse ES cells can differentiate spontaneously, after embryonic body formation, but only a small cell fraction (<0.1%) display β-cell-specific properties, such as staining by zinc chelating dithizone and expression of pancreatic markers at mRNA level [Shiroi, A., et al., *Identification of insulin-producing cells derived from embryonic stem cells by zinc-chelating dithizone Stem Cells*, 2002. 20: p. 284-292].

The approach used by Lumelsky et al. [*Differentiation of embryonic stem cells to insulin-secreting structures similar to pancreatic islets*. Science, 2001. 292(5520): p. 1389-94;] is particularly intriguing. This protocol involved the selection, expansion and differentiation of nestin-expressing cells from ES cell cultures, a strategy previously used to generate neurons. Aggregates of islets-like cells were generated and only a small fraction were insulin-positive cells. However, a re-investigation of the differentiation strategy develop by Lumelsky [Rajagopal, J., et al., *Insulin staining of ES cell progeny from insulin uptake*. Science, 2003. 299: p. 363] with mouse and human ES cell lines showed that insulin positive cells generated by nestin-positive progenitors did not produce insulin but merely absorbed it from the culture medium and were characterized by small condensed nuclei and an apoptotic cell status. Although the differentiated cells were insulin positive, the detection of insulin mRNA was inconsistent, and neither C-peptide, a by-product of insulin synthesis, nor secretor granules were detected.

ES stem cells have been showed to differentiate into insulin-secreting cells by driving and forcing the in vitro differentiation from multipotent cells to endoderm cell precursors and pancreatic cell lineage, and to normalize glucose levels when transplanted in diabetic mouse model [Soria, B., et al., *Insulin-secreting cells derived from embryonic stem cells normalize glycemia in streptozotocin-induced diabetic mice*. Diabetes, 2000. 49(2): p. 157-62.]. Because this approach generated only small amounts of insulin-producing cells, recent studies are attempting to increase the differentiation efficiency of insulin-producing cells by constitutive expression of gene important in pancreas and β-cells development [Soria, B., et al., *Insulin-secreting cells derived from embryonic stem cells normalize glycemia in streptozotocin-induced diabetic mice*. Diabetes, 2000. 49(2): p. 157-62].

In conclusion, mouse and human ES cells display the basic capacity to differentiate into pancreatic insulin-producing cells; however the problems with cell survival, proliferation rate, in vitro culture, freezing and thawing processes are still to be overcome. Problems in the control of differentiation leave the possibility of teratoma formation from ES cell derived insulin-producing cells. In addition existing ES cell lines are not believed to be ideal for generating islets or β-cells. Finally, ethical concerns about the use of ES cells need to be resolved before this technology can be implemented. Clearly there is a need for new approaches for providing cells suitable for transplantation for the treatment of diabetes.

SUMMARY OF THE INVENTION

A first aspect of the present invention is a method of treating diabetes in a mammalian subject in need thereof, comprising the steps of: (a) providing mammalian amniotic fluid stem cells, wherein the cells are optionally differentiated into pancreatic-like cells; and then (b) administering the cells to the subject in an amount effective to treat diabetes. In some embodiments the subject is, preferably, effectively treated for the diabetes for at least two months after the administering step.

In some embodiments the cells are not differentiated into pancreatic-like cells prior to the administering step (e.g., where the cells are administered into the pancreas of the subject); in other embodiments the cells are differentiated into pancreatic-like cells prior to the administering step (e.g., where the cells are differentiated into pancreatic-like cells prior to the administering step by culturing the cells in a medium containing a pancreatic differentiation factor; or where the cells are differentiated into pancreatic-like cells prior to the administering step by expressing a recombinant (i.e., "heterologous") or endogeneous pancreatic differentiation factor therein).

A second aspect of the present invention is a pharmaceutical composition useful for the treatment of diabetes comprising, pancreatic-like cells (e.g., mammalian, particularly human, cells) in a pharmaceutically acceptable carrier, wherein the pancreatic-like cells are differentiated from amniotic fluid stem cells. The carrier may be an an aqueous carrier, and the composition may be provided in unit dosage form, including an injectable composition. In some embodiments the cells are encapsulated in an insulin-permeable capsule; in other embodiments the cells are unencapsulated (e.g., in direct contact with the carrier).

A further aspect of the present invention is the use of cells as described above for the preparation of a medicament for carrying out a method of treatment as described above.

The foregoing and other objects and aspects of the present invention are explained in greater detail in the drawings herein and the specification set forth below.

BRIEF DESCRIPTION OF THE DRAWINGS

The patent or application file contains at least one drawing executed in color. Copies of this patent with color drawing(s) will be provided by the patent and Trademark Office upon request and payment of the necessary fee.

FIG. 1. Morphological changes of mAFSC after adenovirus-Pdx1 infection in vitro. Phase-contrast microscopy at day 20, (A) Mouse amniotic fluid-derived stem cells (mAFSC) infected with adenovirus-LacZ [mAFSC(Ad-LacZ), (B,C) mAFSC infected with adenovirus-Pdx1 [mAFSC(Ad-Pd1)].

FIG. 2. In vitro mAFSC express pancreatic islet markers after 20 days from adenovirus-Pdx1 infection. Peroxidase-staining for PDX1 (A), glucagon (B), insulin (C), Pax6 (D).

FIG. 3. Expression of insulin and glucagon in the pancreatic islets-like structures after 20 days from adenovirus-Pdx1 infection. (A) FITC-glucagon cells are distributed on the periphery and (B) FITC-insulin cells are mostly in the center. (C) Phase-contrast image of pancreatic islet-like structure.

FIG. 4. Expression of Pdx1, Pax6 and Ngn3 after adenovirus-Pdx1 infection. (A) Western Blot analysis for Pdx1 and HA, 48 h after Pdx1 infection. (B) RT-PCR for Pdx1, Ngn3, Pax6 before infection (day 0), and 10, 14 days after adenovirus-Pdx1 infection in vitro.

FIG. 5. Induction of hyperglycemia after STZ-treatment in NOD/SCID mice. (A) i.p. injection of STZ (n=15) 50 mg/kg/d for 3 days resulted in the onset of diabetes at day 7 and in severe hyperglycemia at day 28. NOD/SCID mice (n=10) untreated maintained euglycemia in 28 days. (B) Increased blood glucose correlated with decreased systemic insulin at day 7 and 28 in STZ-treated mice in contrast to untreated mice. n=number of mice. Data are mean±s.e.m.

FIG. 6. Number and morphology of pancreatic islets after STZ-treatment. (A) Number of pancreatic islets after 28 days in control mice (-STZ) and in the STZ-treated mice (+STZ). Quantitative analysis of the number of islet structures for 6 sections of each pancreas. P<0.05. (B,C) H&E staining of pancreatic sections on control mice. (D,E) H&E staining of pancreatic sections in STZ-treated mice: altered islets morphology (D) and few numbers of islets (E).

FIG. 9. Maintaining of euglycemia in STZ-treated mice transplanted with mAFSC(Ad-Pdx1). Follow up: 76 days. (A) Recipient mice receiving mAFSC(Ad-Pdx1) (+STZ+Pdx1 n=5) maintained normal glucose level for 76 days. STZ-treated mice did not show any spontaneous reversion of hyperglycemia (+STZ. 8 mice of 10 dead before 76 days). (B) Glucose tolerance test at day 76 (1 gr/kg glucose i.p.). Control=no STZ-treated mice age-matched (n=5). Treated=diabetic mice transplanted with mAFSC(Ad-Pdx1) (n=5). n=number of mice.

FIG. 10. Number and morphology of pancreatic islets after mAFSC transplantation. (A) Number of pancreatic islets after 3 week from cells transplantation. Pdx1=mAFSC(Ad-Pdx1), LacZ=mAFSC(Ad-LacZ). Quantitative analysis of the pancreatic islets' number for 6 sections of each pancreas (n=5). P<0.05. (B,C) H&E staining for pancreatic islets morphology in mAFSC(Ad-Pdx1) treated-mice. (D,E) H&E staining for mAFSC(Ad-LacZ) treated-mice. n=number of mice.

FIG. 11. H&E and insulin staining after mAFSC transplantation. (A,D) Untreated mice age-matched (n=5). (B,E) STZ-treated mice (n=5): 28 days after STZ injection. (C,F) STZ-treated mice transplanted with mAFSC(Ad-Pdx1): 3 weeks after transplantation (n=5).

FIG. 12. Donor cells engraft in the pancreatic islet unit. Pancreatic section of STZ-treated mouse 3 weeks after mAFSC(Ad-Pdx1) transplantation: FITC-HA.

FIG. 13. Donor cells in the pancreatic islet unit express insulin. Immunofluorescence staining of pancreatic section of recipient mouse three weeks after mAFSC(Ad-Pdx1) transplantation (A) FITC-insulin (B) TEXAS RED-HA (C) FITC-insulin+TEXAS RED-HA.

FIG. 14. Marker expression by mAFS-M1 cells. (A) Oct-4 mRNA by RT-PCR: 1-mouse fibroblasts; 2, 3-mAFS-M1 cells at passages 10 and 18. (B-I) Flow cytometry with monoclonal antibodies [filled] versus isotype controls [empty]. (B) Oct-4. (C) SSEA-1. (D) CD34. (E) CD44. (F) CD45. (G) CD90 (Thy-1). (H) CD105. (I) CD117 (c-Kit). (J) Sca-1. (K) MHC Class I (H2-K, H2-D). (L) MHC Class II.

DETAILED DESCRIPTION OF THE PREFERRED EMBODIMENTS

Figure 7A:
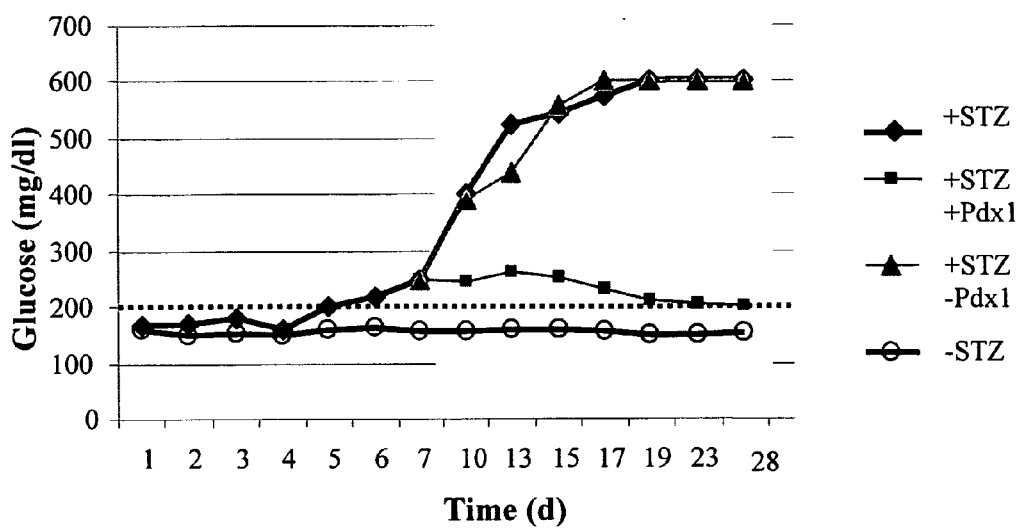
FIG. 7. Prevention of increasing and reduction of blood glucose in onset diabetic mice after transplantation of mAFSC. Follow up: 28 days. (A) Prevention of increasing of blood glucose in onset diabetic mice (cell transplantation at day 7); comparison of blood glucose in STZ-treated mice (+STZ n=15), in control mice −STZ n=10), in mice transplanted with mAFSC(Ad-LacZ) (+STZ−Pdx1 n=10) or mAFSC(Ad-Pdx1) (+STZ+Pdx1 n=10). Normalization of blood glucose occurred in 28 days. n=number of mice. (B) Reduction of blood glucose in severe hyperglycemic mice (cell transplantation at day 10); comparison of blood glucose in STZ-treated mice (+STZ) and in STZ-treated mice transplanted with mAFSC(Ad-Pdx1) (+STZ+Pdx1 n=2). n=number of mice. Data are mean±s.e.m.

"Diabetes" as used herein includes both insulin-dependent diabetes (encompassing patients described as being afflicted with type I diabetes, as well as some other patients) and non-insulin-dependent diabetes (encompassing most patients described as being afflicted with type II diabetes).

"Amniotic fluid stem cell" as used herein refers to a cell, or progeny of a cell, that (a) is found in, or is collected from, mammalian amniotic fluid, mammalian chorionic villus, and/or mammalian placental tissue, or any other suitable tissue or fluid from a mammalian donor, (b) is pluripotent; (c) has substantial proliferative potential, (d) optionally, but preferably, does not require feeder cell layers to grow in vitro, (e) optionally, but preferably, specifically binds c-kit antibodies (particularly at the time of collection, as the ability of the cells to bind c-kit antibodies may be lost over time as the cells are grown in vitro).

"Pancreatic-like cell" as used herein refers to a cell that produces insulin. More particularly pancreatic-like cells are cells that exhibit (a) glucose-dependent insulin release, (b) the presence of insulin positive secretory granules (c) express Pdx1, and preferably also express Pax6 and Ngn3 (eg, as determined by RT-PCR) during early differentiation, and (d) demonstrate the rescue or reduction in symptoms of diabetes in a mouse diabetes model (e.g., as described herein).

"Treat" as used herein refers to any type of treatment that imparts a benefit to a patient afflicted with a disease, including improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

The present invention is primarily concerned with the treatment of human subjects (including both male and female subjects and infant, juvenile, adolescent, adult and geriatric subjects), but the invention may also be carried out on animal subjects, particularly mammalian subjects such as mice, rats, dogs, cats, livestock and horses for veterinary purposes, and for drug screening and drug development purposes.

The disclosures of all United States patent references cited herein are to be incorporated by reference herein in their entirety.

1. Collection and Preparation of Cells.

Amniotic fluid stem cells (AFSCs) useful for carrying out the present invention are known and described in, for example, PCT Application WO 03/042405 to Atala and DeCoppi; In 't Anker, P. S., et al., *Amniotic fluid as a novel source of mesenchymal stem cells for therapeutic transplantation*. Blood, 2003. 102(4): p. 1548-9; Prusa, A. R., et al., *Oct-4-expressing cells in human amniotic fluid: a new source for stem cell research*? Hum Reprod, 2003. 18(7): p. 1489-93; Kaviani, A., et al., *The amniotic fluid as a source of cells for fetal tissue engineering*. J Pediatr Surg, 2001. 36(11): p. 1662-5; Prusa, A. R. and M. Hengstschlager, *Amniotic fluid cells and human stem cell research: a new connection*. Med Sci Monit, 2002. 8(11): p. RA253-7.

In general, AFSCs are cells, or progeny of cells, thate are found in or collected primarily from mammalian amniotic fluid, but may also be collected from mammalian chorionic villus or mammalian placental tissue. The cells are preferably collected during the second trimester of gestation. In mice the cells are most preferably collected during days 11 and 12 of gestation. Preferably the mammalian source is of the same species as the mammalian subject being treated.

In general, the tissue or fluid can be withdrawn by amniocentesis, punch-biopsy, homogenizing the placenta or a portion thereof, or other tissue sampling techniques, in accordance with known techniques. From the sample, stem cells or pluripotent cells may be isolated with the use of a particular marker or selection antibody that specifically binds stem cells, in accordance with known techniques such as affinity binding and/or cell sorting. Particularly suitable is the c-Kit antibody, which specifically binds to the c-kit receptor protein. C-kit antibodies are known (see, e.g., U.S. Pat. Nos. 6,403,559, 6,001,803, and 5,545,533). Particularly preferred is the antibody c-Kit(E-1), a mouse monoclonal IgG that recognizes an epitope corresponding to amino acids 23-322 mapping near the human c-kit N-terminus, available from Santa Cruz Biotechnology, Inc., 2145 Delaware Avenue, Santa Cruz, Calif., USA 95060, under catalog number SC-17806).

AFSCs used to carry out the present invention are pluripotent. Hence, they differentiate, upon appropriate stimulation, into at least osteogenic, adipogenic, myogenic, neurogenic, hematopoitic, and endothelial cells. Appropriate stimulation, for example, may be as follows: Osteogenic induction: The cKit$^+$ cells were cultured in DMEN low glucose with 10% FBS supplementing with 100 nM dexamethasone (Sigma-Aldrich), 10 mM beta-glycerophosphate (Sigma-Aldrich) and 0.05 mM ascorbic acid-2-phosphate (Wako Chemicals, Irving, Tex.); Adipogenic induction: To promote adipogenic differentiation, we cultured c-Kit$^+$, seeded at density of 3000 cells/cm$^2$ in DMEN low glucose medium with 10% FBS supplemented with 1 μM dexamethasone, 1 mM 3-isobutyl-1-methylxantine, 10 μg/ml insulin and 60 μM indomethacin (all from Sigma-Aldrich); Myogenic induction: c-Kit$^+$ cells were plated into Matrigel-precoated dish (1 mg/ml, Collaborative Biomedical Products) and cultured in myogenic medium (DMEN low glucose supplemented with 10% horse serum, and 0.5% chick embryo extract from Gibco) followed by treatment of 5-azacytidine (10 μM, Sigma) added in myogenic medium for 24 h; Endothelial induction: c-Kit$^+$ cells were plated into gelatin-precoated dish and cultured in endothelial basal medium-2 (EBM-2, Clonetics BioWittaker) supplemented with 10% FBS and 1% glutamine (Gibco). In preferred embodiments no feeder layer or leukaemia inhibitory factor (LIF) are required either for expansion or maintenance of AFSCs in the entire culture process.

In addition the AFSCs differentiate into pancreatic-like cells, as disclosed herein below.

AFSCs also have substantial proliferative potential. For example, they proliferate through at least 60 or 80 population doublings or more when grown in vitro. In preferred embodiments of AFSCs used to carry out the invention proliferate through 100, 200 or 300 population doublings or more when grown in vitro. In vitro growth conditions for such determinations may be: (a) placing of the amniotic fluid or other crude cell-containing fraction from the mammalian source onto a 24 well Petri dish a culture medium [α-MEM (Gibco) containing 15% ES-FBS, 1% glutamine and 1% Pen/Strept from Gibco supplemented with 18% Chang B and 2% Chang C from Irvine Scientific], upon which the cells are grown to the confluence, (b) dissociating the cells by 0.05% trypsin/EDTA (Gibco), (c) isolating an AFSC subpopulation based on expression of a cell marker c-Kit using mini-MACS (Mitenyl Biotec Inc.), (d) plating of cells onto a Petri dish at a density of $3-8\times10^3/cm^2$, and (e) maintaining the cells in culture medium for more than the desired time or number of population doublings.

Preferably, the AFSCs are also characterized by the ability to be grown in vitro without the need for feeder cells (as described in PCT Application WO 03/042405 to Atala and DeCoppi. In preferred embodiments undifferentiated AFSCs stop proliferating when grown to confluence in vivo.

AFSCs used to carry out the present invention are preferably positive for alkaline phosphatase, preferably positive for Thy-1, and preferably positive for Oct4, all of which are known markers for embryonic stem cells, and all of which can be detected in accordance with known techniques. See, e.g., Rossant, J., *Stem cells from the Mammalian blastocyst*. Stem Cells, 2001. 19(6): p. 477-82; Prusa, A. R., et al., *Oct-4-expressing cells in human amniotic fluid: a new source for stem cell research?* Hum Reprod, 2003. 18(7): p. 1489-93.

In a particularly preferred embodiment, the AFSCs do not form a teratoma when undifferentiated AFSCs are grown in vivo. For example, undifferentiated AFSCs do not form a teratoma within one or two months after intraarterial injection into a 6-8 week old mouse at a dose of $5\times10^6$ cells per mouse.

In preferred embodiments the amniotic fluid stem cells used to carry out the present invention express several markers characteristic of ES cells and/or various multipotent adult stem cells. These include the transcription factor Oct-4 (Pou5f1), SSEA-1 (Stage Specific Embryonic Antigen 1), Sca-1 (Ly-6A/E), CD90 (Thy-1), and CD44 (Hyaluronate receptor. Ly-24, Pgp-1).

In preferred embodiments the amniotic fluid stem cells used to carry out the present invention do not express CD34 and CD105, markers of certain lineage restricted progenitors, nor the hematopoietic marker CD45.

In preferred embodiments the amniotic fluid stem cells used to carry out the present invention express low levels of major histocompatibility (MHC) Class I antigens and are negative for MHC Class II.

When desired, differentiation of cells to pancreatic-like cells can be carried out in accordance with any of a variety of known techniques. "Differentiation" and "differentiating" as used herein include both (a) treatment of the cells to induce differentiation and completion of differentiation of the cells in response to such treatment, both prior to administration to the subject, as well as (b) treatment of the cells to induce differentiation, then administration of the cells to a subject, and then differentiation of the cells in response to such treatment after they have been administered to a subject.

For example, the cells can be contacted to or cultured in a conditioning media such as described in US Patent Application 2002/0182728 (e.g., a medium that comprises Dulbecco's Minimal Essential Medium (DMEM) with high glucose and sodium pyruvate, bovine serum albumin, 2-mercaptoethanol, fetal calf serum (FCS), penicillin and streptomycin (Pen-Strep), and insulin, transferrin and selenium). In another example, the cells may be treated with a cAMP upregulating agent to induce differentiation as described in U.S. Pat. No. 6,610,535 to Lu. In still another example, the cells may be grown in a reprogramming media, such as described in US Patent Application 2003/0046722A1 to Collas to induce differentiation to a pancreatic cell type.

In another embodiment, differentiation may be carried out using the 5 steps protocol describe by Lumelsky at al. Lumelsky, N., et al., *Differentiation of embryonic stem cells to insulin-secreting structures similar to pancreatic islets*. Science, 2001. 292(5520): p. 1389-94.

In another embodiment, differentiation may be carried out using DMSO to induce pancreatic differentiation in vitro. She-Hoon Oh et al, *Adult bone marrow-derived cells transdifferentiating into insulin-producing cells for the treatment of type I diabetes*. Lab Inv, 2004, 84: 607-617

In another embodiment, differentiation may be carried out using Nicotinamide to induce pancreatic differentiation in vitro. See, e.g., Otonkoski, T., et al, *Nicotinamide is a potent inducer of endocrine differentiation in cultured human fetal pancreatic cells*. J Clin Invest, 1993, 92(3): 1459-1466.

In another embodiment, differentation may be carried out using inhibitors of phosphoinositide 3-kinase (PI3K), such as LY294002, to induce pancreatic differentiation in vitro. See, e.g., Hori, Y., et al., *Growth inhibitor promote differentiation of insulin-producing tissue from embryonic stem cells*. PNAS, 2002, 99:16105-16110.

In another embodiment Exendin-4, a naturally occurring 39-amino acid peptide originally isolated from the salivary secretions of the Lizard Heloderma suspectum, can be used to induce pancreatic differentiation in vitro. Nielsen, L L., et al., *Pharmacology of exenatide (synthetic exendin-4): a potential therapeutic for improved glycemic control of type 2 diabetes*. Regul Pept. 2004 Feb 15; 117(2):77-88. Review.

In still another embodiment, anti-sonic hedgehog (Anti-Shh) and co-culturing with pancreatic rudiments can be used to induce pancreatic differentiation in vitro. Leon-Quinto, T., et al., *In vitro direct differentiation of mouse embryonic stem cells into insulin-producing cells*. Diabetologia, 2004, 47:1442-1451.

In one preferred embodiment the differenting step is carried out by transducing (sometimes also referred to as "engineering" or "transforming") the cells with a vector, or introducing into the cells a vector, that contains a nucleic acid encoding a differentiation factor (such as Pdx1, Ngn3, Nkx6.1, Nkx2.1, Pax6, or Pax4) and expresses the differentiation factor in the cells, or by activating the expression of an endogeneous nucleic acid encoding a differentiation factor in the cells (e.g., engineering the cells to activate transcription of an endogeneous differentiation factor such as Pdx1, Ngn3, Nkx6.1, Nkx2.1, Pax6, or Pax4, such as by inserting a heterologous promoter in operative associated with an endogeneous differentiation factor, in accordance with known techniques. See, e.g., U.S. Pat. No. 5,618,698). Such exogenous nucleic acids may be of any suitable source, typically mammalian, including but not limited to rodent (mouse, hamster, rat), dog, cat, primate (human, monkey), etc.

For recombinant techniques any suitable vector may be used, including plasmids, cosmids, bacteriophages, DNA viruses, RNA viruses and retroviruses, all of which are known for the expression of a heterologous nucleic acid in stem cells, progenitor cells, etc., in substantially the same manner as known. See, e.g., U.S. Pat. Nos. 6,392,118; 6,309,883; 6,258,354; and 4,959,313. Such adenovirus vectors are also known and can be utilized with AFSCs as described herein in accordance with known techniques. See, e.g., U.S. Pat. Nos. 6,544,780; 6,503,498; 5,981,225; and 5,670,488; Since transient expression is useful in carrying out the present invention, the vector may be simply "naked", or linear, DNA. The recombinant vector containins a nucleic acid encoding the pancreatic differentiation factor, and the differentiation factor may be transiently expressed or stably expressed in the cell. Any suitable pancreatic differentiation factor may be used, with Pdx1 currently preferred. Vectors containing Pdx-1 are known. See, e.g., U.S. Pat. No. 6,774,120. The vector should include a suitable promoter (such as an SV40 promoter, retrovirus LTR-promoter, or cytomegalovirus (CMV) promoter), operatively associated with the nucleic acid to constituitively express, or inducibly express, the differentiation factor in the cells. Expression may be stable expression or transient expression depending upon the specific system chosen, with transient expression currently preferred.

The cells can be protected from immune rejection by modifying cell expression of selected proteins in accordance with known techniques. See, e.g., US Patent Application 2002/0182728. For example, the cultured transdifferentiated cells can be transformed to express a protein or peptide which will inhibit or prevent the destructive immune process. Other useful proteins or peptides may be expressed. In addition, expression of autoantigens specific to the IDD process, such as GAD, 64 kD islet cell surface antigens, to the extent they may be expressed by the transdifferentiated cells, or any other markers identified on the cells, can be eliminated by standard gene knock-out or selection procedures to produce cells which are not or are less susceptible to autoimmune attack. Methods for producing such mutant or knock out cells are well known in the art and include, for example, homologous recombination methods disclosed in U.S. Pat. Nos. 5,286,632; 5,320,962; 5,342,761; and in WO 90/11354; WO 92/03917; WO 93/04169; WO 95/17911, all of which are herein incorporated in their entirety by reference. In addition, a universal donor cell is produced by preparing transdifferentiated cells modified so as not to express human leukocyte antigen (HLA) markers.

If desired the cells can be frozen or cryopreserved prior to use, and then thawed to a viable form. Methods of freezing or cryopreserving cells (for subsequent return to viable form) are well known in the art. For example, cryopreservation of cells can involve freezing the cells in a mixture of a growth medium and another liquid that prevents water from forming ice crystals, and then storing the cells at liquid nitrogen temperatures (e.g., from about −80 to about −196° C.). See, e.g., U.S. Pat. No. 6,783,964 to Opara.

2. Formulations and Administration.

The cells described above may be formulated for administration in a pharmaceutical carrier in accordance with known techniques. See, e.g., Hariri, US Patent Application 2003/0180289; Remington, *The Science And Practice of Pharmacy* (9th Ed. 1995). In the manufacture of a pharmaceutical formulation according to the invention, the cells are typically admixed with, inter alia, an acceptable carrier. The carrier must, of course, be acceptable in the sense of being compatible with any other ingredients in the formulation and must not be deleterious to the patient. The carrier may be a solid or a liquid, or both (e.g., hydrogels), and may be formulated with the cells as a unit-dose formulation. In one embodiment the cells are provided as a suspension in the carrier to reduce clumping of the cells.

The cells can be formulated in unencapsulated form (e.g., with the cell membranes in direct contact with the pharmaceutical carrier, and subsequently in direct contact with immune cells of the subject after administration) or in encapsulated form (e.g., encapsulated in an insulin-permeable capsule that also is permeable to nutrients and oxygen to sustain the viability of the cells in vivo). Materials and methods for the encapsulation of cells in insulin-permeable capsules are well known and described in, for example, U.S. Pat. No. 6,783,964 to Opara. For example, the cells may be encapsulated in a microcapsule of from 50 or 100 μm to 1 or 2 mm in diameter that comprises an internal cell-containing core of polysaccharide gum surrounded by a semipermeable membrane; a microcapsule that comprises alginate in combination with polylysine, polyornithine, and combinations thereof. Other suitable encapsulating materials include but are not limited to those described in U.S. Pat. No. 5,702,444 to Struthers et al.

The formulations of the invention include those for parenteral administration (e.g., subcutaneous, intramuscular, intradermal, intravenous, intraarterial, or intraperitoneal injection). Intravenous and intraarterial injection are currently preferred.

In one embodiment the administration step is carried out intravascularly, either by simple injection, or by injection through a catheter positioned in a suitable blood vessel, such as a pancreatic artery.

Formulations of the present invention suitable for parenteral administration comprise sterile liquid, preferably aqueous, injection compositions of the cells, which preparations may be isotonic with the blood of the intended recipient. These preparations may contain anti-oxidants, buffers, bacteriostats and solutes which render the formulation isotonic with the blood of the intended recipient. The preparations are, apart from the cells being administered, sterile in the sense that they are free of microbial contaminants such as bacteria and viruses.

The formulations can be in a synringeable, injectable form, can be in a form suitable for surgical implantation, e.g., into the pancreas of a subject, or in any other form suitable for administration into the patient.

The cells administered to the subject may be allogenic (of the same species), xenogenic (of a different species) or xenogenic (of the same species and genetic makeup) as the subject to which the cells are administered, depending upon other steps such as the presence or absence of encapsulation or the administration of immune supression therapy of the cells.

The therapeutically effective dosage of cells will vary somewhat from patient to patient, and will depend upon factors such as the age, weight, and condition of the subject and the route of delivery. Such dosages can be determined in accordance with procedures known to those skilled in the art. In general, in some embodiments, a dosage of $1\times10^5$, $1\times10^6$ or $5\times10^6$ up to $1\times10^7$, $1\times10^8$ or $1\times10^9$ cells or more per subject may be given, administered together at a single time or given as several subdivided administrations. In other embodiments a dosage of between $1\text{-}100\times10^8$ cells per kilogram subject body weight may be given, administered together at a single time or given as several subdivided administration. It is preferred that, once administered (as a single dose or after the last of several doses) the subjects are effectively treated for said diabetes for at least two or three months, or even more preferably for at least two or three years, after the administration of the dosage of cells (e.g., as determined by blood glucose testing). Of course, follow-up administrations may if necessary be given.

If desired or necessary, the subject may be administered an agent for inhibiting transplant rejection of the administered cells, such as rapamycin, azathioprine, corticosteroids, cyclosporin and/or FK506, in accordance with known techniques. See, e.g., R. Calne, U.S. Pat. Nos. 5,461,058; 5,403,833; 5,100,899; see also U.S. Pat. Nos. 6,455,518; 6,346,243; and 5,321,043.

The present invention is explained in greater detail in the following non-limiting Examples.

Experimental

These experiments show that mouse amniotic fluid stem cells (mAFSC) can be induced to differentiate to a pancreatic cell phenotype in culture and in vivo, by transient expression of a master regulator of pancreatic differentiation, the pancreas duodenal homeobox gene (Pdx1), driven in a constitutive promoter (pCMV from cytomegalovirus) in a defective adenovirus vector. We also note that the order of the expression of genes for the transcription factors Pax6 and Ngn3 during in vitro differentiation is consistent with the reported developmental program in the mouse embryo.

A. In Vitro Methods

Generation of adenovirus vectors. The hamster pancreatic duodenal homeobox gene 1 (Pdx1) was placed under the control of cytomegalovirus (CMV) early promoter/enhancer region by inserting the complete cDNA of each gene into the pShuttle2 vector. The vector was excised and legated to pAdeno-X (BD Biosciences Clontech). A peptide tag (a hemagglutinin epitope, HA) was incorporated in the carboxyl terminus of the vector-encoded Pdx1. A similar construct with LacZ gene served as a negative control. The Pdx1 vector used for this experiment was graciously provided by Dr. Raghu Mirmira of the University of Virginia.

Cell culture and differentiation conditions. Mouse amniotic fluid was collected from 11.5 days pregnant female C57BL/6J mice aging from 4 to 6 weeks under light microscopy using 30 gauge needles. We isolated a subpopulation based on expression of the stem cell marker c-Kit using mini-MACS (Mitenyl Biotec Inc.). Mouse amniotic fluid stem cells were cultured in Petri dishes in culture medium [α-MEM (Gibco) containing 15% ES-FBS, 1% glutamine and 1% Pen/Strept from Gibco supplemented with 18% Chang B and 2% Chang C from Irvine Scientific]. mAFSC (6000 cells/cm$^2$) were plated in matrigel-precoated dishes and infected with recombinant adenovirus vector carrying Pdx1-HA. Cells infected with recombinant adenovirus vector carrying LacZ gene were used as control. Within 7 days in α-medium modified the cells were dissociated by 0.05% trypsin/EDTA (Gibco) for 3 min, collected by centrifugation and re-plated onto poly-L-ornithine-precoated dishes (15 μg/ml) in ES basal medium (KO-DMEN, 1% glutamine, 1% NEAA, 0.1 mM β-mercaptoethanol) supplement with N2 (100×), B27 (50×), bFGF-recombinant human 25 ng/ml (StemCell Technologies). The medium was changed every two days.

Immunostaining. Cells were fixed with 4% paraformaldehyde. The immunohistochemistry analyses were performed with the following primary antibodies: goat polyclonal against Pdx1 (1:50) and glucagon (1:50), rabbit polyclonal anti-Pax6 (1:50) and somatostatin (1:50) from Santa Cruz Biotechnology, and mouse monoclonal anti insulin (1:1000 Sigma-Aldrich). The labeled cells were detected with peroxidase staining (Vectastain ABC, Vector), or biotin-conjugated secondary antibodies with avidin-FITC (Vector).

Western Blotting. In order to evaluate the expression of chimeric PDX1-HA protein (45 kDa), western blot was performed after 48 h from the cell infection, using the following primary antibodies: goat anti-PDX1 (1:1000) and mouse monoclonal anti-HA (1:10000).

RT-PCR analysis. Total cellular mRNA of mAFSC infected with Pdx1 were reverse transcribed, amplified by PCR, electrophoretically separated and analyzed using standard protocols at day 0, 7, 14 during in vitro differentiation. Primers sequence and fragment size are listed in the Table below.

| Gene | Primer (sense-antisense) | | Segment length (bp) |
|---|---|---|---|
| Pax6 | 5'CAGTCACAGCGGAGTGAATC3' | (SEQ ID NO: 1) | 658 |
|  | 5'CGTTCAGCTGAAGTCGCAT3' | (SEQ ID NO: 2) |  |
| Ngn3 | 5'TGGCACTCAGCAAACAGCGA3' | (SEQ ID NO: 3) | 444 |
|  | 5'ACCCAGAGCCAGACAGGTCT3' | (SEQ ID NO: 4) |  |
| Pdx1 | 5'TGTAGGCAGTACGGGTCCTC3' | (SEQ ID NO: 5) | 325 |
|  | 5'CTCGAACATTTGACCCCACC3' | (SEQ ID NO: 6) |  |

B. In Vivo Methods

Animal Model. Immune-deficient NOD/SCID mice (The Jackson Laboratories) 6-8 weeks of age were injected intraperitoneally with 50 mg/kg streptozotocine (STZ) (Sigma-Aldrich) daily for days 1-3. STZ was solubilized in Na-citrate buffer, Ph 4.5, and injected within 15 min of preparation in fasted mice.

Blood glucose was measured in unfasted mice between 9:00 and 11:00 AM daily for the first 7 days and three time a week from day 7 to 28 and twice a week from day 28 and 76. Peripherical blood (100 μl) was collected on day 0, 7, 28 and 76 and serum insulin was quantified with mouse insulin specific immunoassay (Mercodia).

Cell Transplantation. We separated the STZ-treated NOD/SCID mice in two groups at day 7: one received mAFSC infected with adenovirus carrying LacZ-gene and one received mAFSC infected with adenovirus-Pdx1-HA. The cell number was between 5×10$^5$ and 10$^6$. The cells were transplanted with one intra-left ventricle injection using a 30 gauge needle. At day 7 all the STZ-treated mice showed blood glucose level >200 mg/dl in two different measurement. 5 mice for each group were sacrificed at day 28 and other 5 mice for each group were followed until day 76.

Day 28 was chosen because all STZ-treated mice presented severe hyperglycemia and almost totally destruction of pancreatic islets and in order to detect the transplanted cells in the recipient mouse (transient expression of adenovirus). We chose day 76 because at this time point all the STZ-treated mice did not show any spontaneous reversion of hyperglycemia.

Another group of mice (n=2) were transplanted at day 10 when they all showed severe hyperglycemia (500-600 mg/dl).

Glucose tolerance test. Mice fasted for 6 h were injected i.p. with glucose in saline at 1 mg per g of body weight. Blood glucose levels were monitored at 0, 5, 15, 30, 60, 120, 180, and 240 min in samples obtained from the tail vein.

Immunohistochemistry. Pancreas was embedded in frozen tissue embedding gel (Sakura). Serial sagittal cryogenic sections were cut at a thickness of 6 μm for above 1 mm. 6 sections of each pancreas, separated by 180 μm were stained with H&E to check the pancreatic islets number and morphology after STZ treatment and subsequent transplantation. Another 6 sections for each pancreas were chosen for immune-staining; sections were stained with mouse monoclonal anti-insulin (1:1000 Sigma-Aldrich), mouse monoclonal anti-HA clone HA-7 (1:1000 Sigma-Aldrich). Insulin labeled cells were visualized with peroxidase-staining (Vectastain ABC reagent, Vector) and biotin-conjugated secondary antibodies with Avidin-FITC (Vector). Ha labeled cells were visualized with a biotin-conjugated secondary antibody with Avidin-FITC (Vector), or TEXAS RED (Vector).

Statistical analysis. Blood glucose and serum insulin concentrations were shown as the mean±s.e.m. for mice grouped by transplanted cell populations or STZ treated. Statistical analysis for significance was done with a two-tailed student's t-test.

C. Results

Differentiation of mouse amniotic fluid-derived stem cells into pancreatic-like cells. Within 7 days in culture mAFSC infected with adenovirus-Pdx1 [mAFSC(Ad-Pdx1)] started change in round shape and growing in cluster (FIG. 1B,C). Within 20 days in culture the progenitor cell expressed Pdx1 (FIG. 2A), Pax6 (FIG. 2C), glucagon (FIG. 2B) and insulin (FIG. 2D). The cell did not express somatostatin and PP (data not show). We found that the majority of glucagons positive cells surround the insulin-positive cells (FIG. 3). mAFSC infected with LacZ gene [mAFSC(Ad-LacZ)] did not show any change at day 7 and they could not survive in serum-free medium at day 20 (data not show).

Previous experiments to assess the in vitro culture conditions showed that absence of matrigel in the first week of differentiation results in significant reduction of insulin expressing cell number at 20 days.

The expression of chimeric PDX1-HA protein was confirmed by western blotting (FIG. 4A). RT-PCR analysis showed expression not only of Pdx1, but also of genes for the transcription factors Ngn3 and Pax6 (FIG. 4B), important pro-endocrine genes during pancreas development. Not one of these genes was expressed in mAFSC infected with the control vector. Pax6 was expressed higher at day 10 after Pdx1 transduction than at day 14, while Ngn3 increased from day 10 to 14.

Insulin-dependent diabetic mouse model. To evaluate the potential capability of mouse amniotic fluid-derived stem cells to restore tissue function after injury, we adopted a mouse model of streptozotocine-induced pancreatic damage. 15 STZ-treated mice showed onset-diabetes at day 7 and severe hyperglycemia (>600 mg/dl) (FIG. 4A) with a mortality of 50% at day 28. 10 NOD/SCID mice (control group) did not show any blood glucose increase in 28 days (FIG. 5A). Increased blood glucose levels were correlated with marked reduction in serum insulin by day 7 until day 28 (FIG. 5B). No spontaneous reversion of hyperglycemia was seen at 76 days in STZ-treated mice using this protocol. 10 NOD/SCID mice (control group) maintained euglycemia and normal insulin level in 76 days.

Morphological assessment of pancreatic sections stained for H&E at day 28 showed that pancreatic damage by STZ was associated with a severe decrease of pancreatic islets' number (8±2/6 pancreatic section per pancreas. P<0.05%); four weeks after STZ treatment, the pancreata of treated animals contained approximately one-fourth the number of islets present in the control mice not exposed to STZ (29±3.5/6 sections. P<0.05) (FIG. 6A). In addition the pancreas of STZ-treated mice (FIG. 6D,E) showed alteration of pancreatic islet morphology in comparison to the control group (FIG. 6B,C).

Figure 8A:
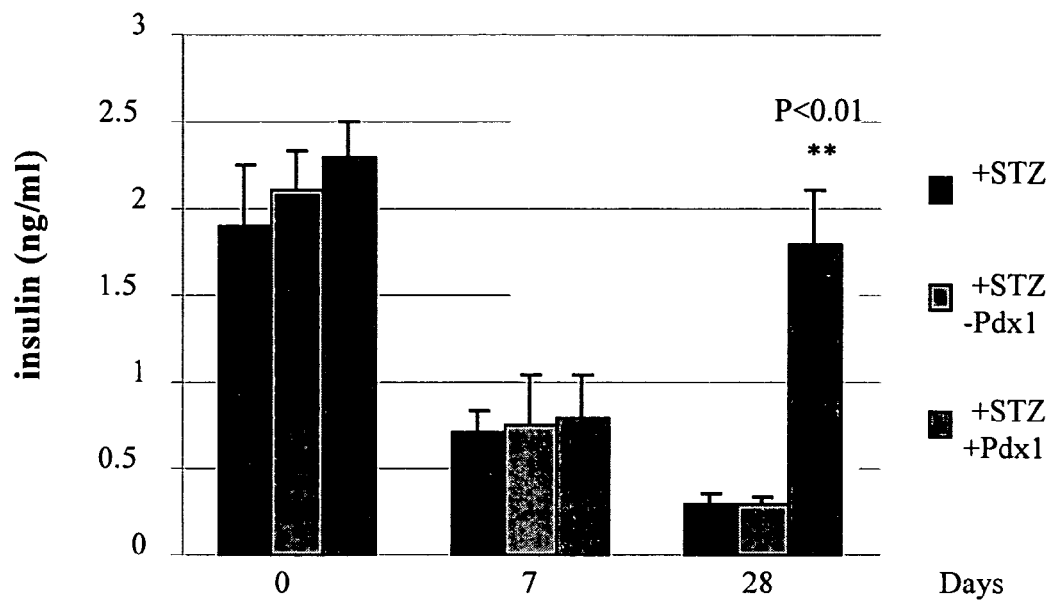
FIG. 8. Reduction of blood glucose correlated with increasing of systemic insulin and with maintaining of body weight after transplantation of mAFSC. (A) Comparison of serum insulin in STZ-treated mice (STZ n=2), in hyperglycemic mice transplanted with mAFSC(Ad-LacZ) (+STZ−Pdx1 n=2) or mAFSC(Ad-Pdx1) (+STZ+Pdx1 n=2). (B) Recipient mice receiving mAFSC(Ad-Pdx1) (+STZ+Pdx1. n=10) maintained body weight comparing with the STZ-treated mice with (+STZ−Pdx1. n=10) or without (+STZ. n=15) mAFSC transplantation. n=number of mice.

Mouse amniotic fluid-derived stem cells reverse diabetic phenotype. We transplanted mouse amniotic fluid cells directly in the arterial circulation, with one intra-left ventricle injection of about $5\times10^5$-$10^6$ cells each mouse. Hyperglycemic mice transplanted with mAFSC(Ad-Pdx1) showed prevention of increasing blood glucose levels after only 3 days from the injection (FIG. 7A) and reduction of hyperglycemia to euglycemia in 28 days (FIG. 7A). The blood glucose reduction was correlated with insulin increasing at day 28 (FIG. 8A). The recipient mice receiving mAFSC(Ad-LacZ) showed high blood glucose level after 3 days and maintained severe hyperglycemia in 28 days (FIG. 7A). Four of ten mice died before 28 days.

Figure 8B:
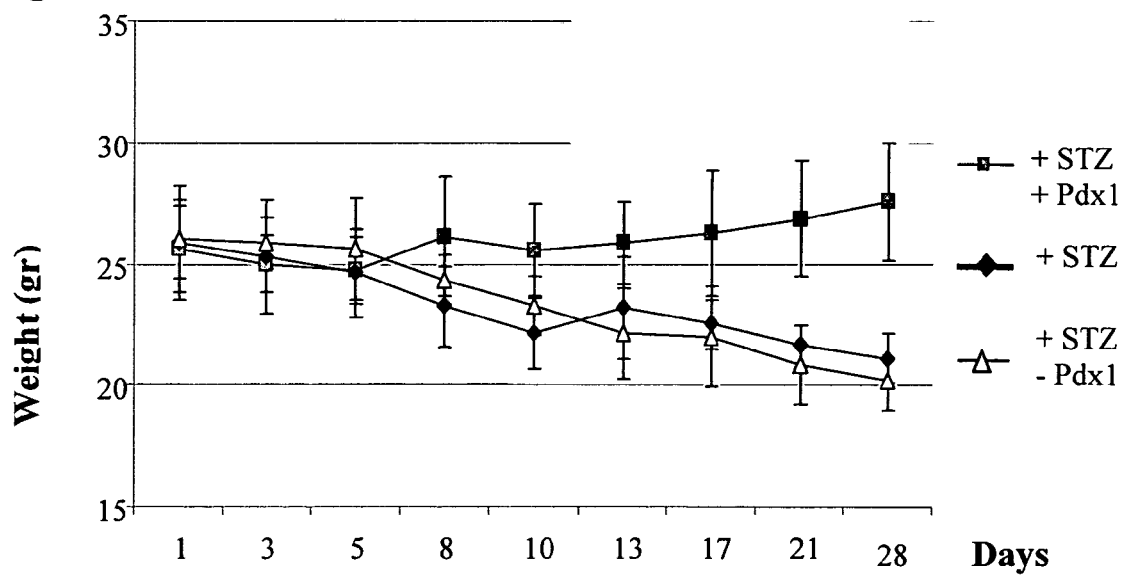

Blood glucose reduction and insulin increasing were correlated with body weight maintaining in the recipient receiving mAFSC(Ad-Pdx1) (FIG. 8B). At day 76 the 5 recipient mice transplanted with mAFSC(Ad-Pdx1) maintained euglycemia (FIG. 9A). Only one mouse receiving mAFSC(Ad-LacZ) survived and showed severe hyperglycemia and hypoinsulinemia (data not show). To evaluated if diabetic mice treated with mAFSC(Ad-Pdx1) were able to not only maintain acceptable glucose levels but also respond physiologically to blood glucose changing, a glucose tolerance test was at day 76 (FIG. 9B). The 5 recipient mice transplanted with mAFSC(Ad–Pdx1) showed a normal glucose reduction in 2 h compared to the no STZ-treated age-match NOD/SCID mice.

Figure 7B:
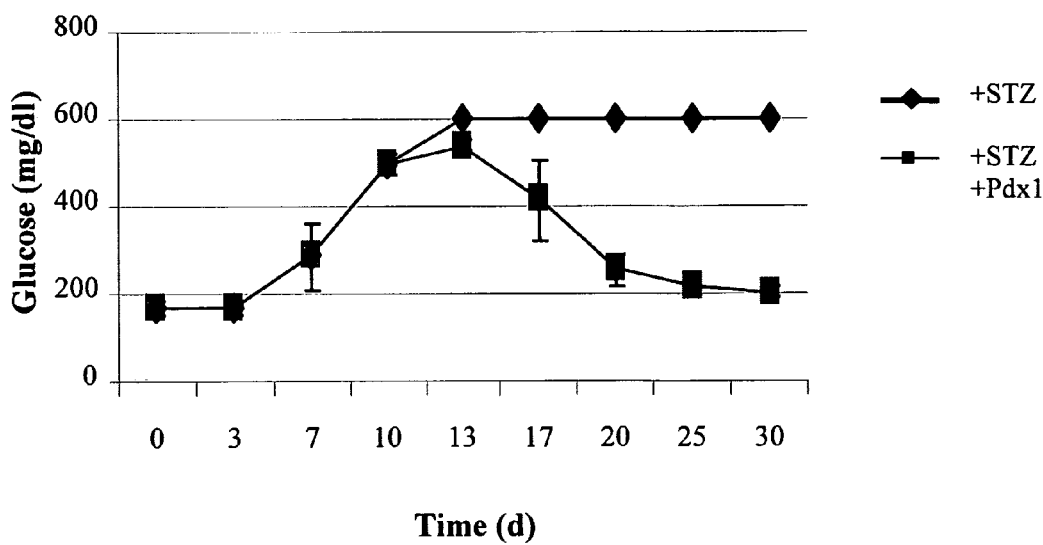

In our experimental design we showed the capability of mouse amniotic fluid-derived stem cell expressing Pdx1 to prevent the increasing and restore normal glucose level if inject in onset diabetic recipient mice (blood glucose level between 200-250 mg/dl). Furthermore, cell therapy with mAFSC(Ad-Pdx1) reverse the diabetic phenotype in mice that received cells after serum glucose reached near maximal level (cell infusion on day 10) (FIG. 7B).

Mouse amniotic fluid-derived stem cells engraft pancreatic islets. Immunohistochemical analyses were performed to characterize pancreatic engraftment at day 28. Cryogenic sections were stained with H&E and insulin to check the pancreatic islets' number and morphology. Three weeks after cell injection the pancreata of animals that received mAFSC transduced with Ad-Pdx1 showed approximately the same number of islets as controls not treated with STZ (25±2/6 sections for pancreas. P<0.05. FIG. 10A) and normal pancreatic islets' morphology (FIG. 10B,C). Injection of mAFSC (Ad-LacZ) significantly decreased the number of pancreatic islets (8±2.5/6 sections. P<0.05. FIG. 10A) and showed abnormal morphology (FIG. 10D,E). The pancreatic islets of diabetic mice treated with mAFSC(Ad-Pdx1) presented normal insulin expression (FIG. 11C,F) comparing with the control animal (FIG. 11A,D). The diabetic mice treated with mAFSC(Ad-LacZ) showed strong reduction in insulin expression (FIG. 11B,E).

We determined whether the differentiated cells derived from donor cells by staining for a hemoagglutinin epitope (HA). We showed that cells expressing HA were located in the pancreatic islets area and (FIG. 12) were co-expressed insulin (FIG. 13). This result shows the contribution in pancreatic islets regeneration by partially replacement of pancreatic β-cells of the recipient with the donor cells.

Mouse amniotic fluid-derived stem cells do not generate teratoma in vivo. Five STZ-treated mice transplanted with mAFSC(Ad-Pdx1) and five transplanted with mAFSC(Ad-LacZ) were analyzed at day 28 for tumors formation. No teratoma formation was detected in any organs of these 10 animals.

D. Conclusions

These data demonstrate that mAFSCs can be induced to differentiate to a phenotype strongly resembling that of pancreatic β-cells in culture and in vivo. Efficient β-cell differentiation was obtained in response to transient expression of Pdx1. The mAFSC transduced with constitutive Pdx1 and maintained in culture for 20 days demonstrated robust expression of insulin, which was not seen with the control vector.

Pdx1 has been reported to regulated islet development, and also to direct stimulated expression of insulin gene. To determine wherever mAFSCs are induced by Pdx1 to enter a differentiation program similar to that in the normal pancreatic development, we examined the expression of genes encoding several transcription factors associated with the normal generation of β-cells in the embryo [Soria, B., *In-vitro differentiation of pancreatic β-cells*. Differentiation, 2001. 68: p. 205-219]. RT-PCR analysis revealed the expression not only of Pdx1, but also of genes for the transcription factors Pax6 and Ngn3 [Soria, B., *In-vitro differentiation of pancreatic β-cells*. Differentiation, 2001. 68: p. 205-219]. Immune staining confirmed the expression of Pax6. Not one of these genes was expressed detectably in mAFSC before infection with adenovirus-Pdx1 and after infection with the control vector. We note that the order of the expression of Pax6 and Ngn3 is consistent with the reported developmental program in the mouse embryo; Pax6 expression was higher at day 10 after Pdx1 transduction than at day 14, while Ngn3 increased from day 10 to day 14. This is evidence that transient expression of Pdx1 in mAFSC can induce the sequential cascade of transcriptional factors involved in the pancreas development. In particular, Pax6 and Ngn3 function as important pro-endocrine factors in the developing pancreas.

We also assessed the efficacy of amniotic fluid stem cells in a type I diabetic mouse model. We tested the ability of mAFSC treated with Pdx1 vector [mAFSC(ad-Pdx1)] to restore pancreatic function after injury by injecting cells into the circulation of hyperglycemic, immune deficient NOD/SCID mice treated with streptozotocine to destroy pancreatic β-cells. The mAFSC were infected with the Pdx1 expression vector, and one day later $5\times10^5$-$10^6$ mAFSC(ad-Pdx1) were administrated to STZ-treated mice. Administration of the cells 7 days after initiation of STZ treatment, at a time when the serum glucose level begins to rise, prevented the onset of diabetic symptoms. Treatment with control mAFSCs, infected by an Ad vector without Pdx1, did not prevent the marked rise in blood glucose. Furthermore, cell therapy with mAFSC(Ad-Pdx1) reversed the diabetic phenotype in mice that received cells after serum glucose reached maximal levels. In our experiments 50% of the STZ-mice died within 3 weeks, and very few survivors showed any significant normalization of blood glucose level in two months. By contrast, mice that received mAFSC(Ad-Pdx1) remained euglycemic for more than two months.

We assessed the generation of pancreatic islets by Pdx1 transduced mAFSCs in vivo both by conventional histology and by staining with antibodies to specific markers. Furthermore, we determined whether the differentiated cells derived from the donor cells by staining for a peptide tag (a hemagglutinin epitope, HA) incorporated at the carboxyl terminus of the vector encoding Pdx1. Because the Ad vector does not integrate, expression of HA-marked Pdx1 can be lost as cells proliferate. However, positive staining of a cell for HA gives definitive evidence for its donor origin.

As shown, STZ treatment severely decreased the number of pancreatic islets in NOD/SCID mice; four weeks after beginning to receive the drug, the pancreata of treated animals contained approximately one-fourth the number of islets present in the control animals not expose to STZ. Injection of mAFSC without Pdx1 did not significantly increase the number of the islets observed in STZ-treated, diabetic mice, the cells did not "home" to the pancreas, and did not contribute to pancreatic islets regeneration. Strikingly, three weeks after cells injection the pancreata of animals that received mAFSC (Ad-Pdx1) showed approximately the same number of islets as control mice that had not been treated with STZ. Most significantly, part of the islets in the STZ-treated mice injected with mAFSC(Ad-Pdx1) appear to derive from the engraftment of donor stem cells, in particular the insulin-producing β-cells.

These data show that murine amniotic-fluid derived stem cells, influenced by the expression of transcription factor Pdx1, actually differentiate to produce pancreatic islets containing functional β-cells. This distinguishes mAFSC from various other stem cell populations (such as bone marrow stem cells) that appear to promote recovery in the animal models of diabetes primarily by supporting the regeneration of residual host cells.

Marker Analysis

The mouse amniotic fluid stem cells (mAFS-M1 cells) used in the experiments described above express several markers characteristic of ES cells and/or various multipotent adult stem cells (FIG. 14). These include the transcription factor Oct-4 (Pou5f1), SSEA-1 (Stage Specific Embryonic Antigen 1), Sca-1 (Ly-6A/E), CD90 (Thy-1), and CD44 (Hyaluronate receptor. Ly-24, Pgp-1). The cells do not express CD34 and CD105, markers of certain lineage restricted progenitors, nor the hematopoietic marker CD45. They express low levels of major histocompatibility (MHC) Class I antigens and are negative for MHC Class II. After expansion in culture the cells lost expression of CD117. Like human AFS cells (7), the murine AFS cells can be induced to differentiate in vitro along the osteoblastic, adipogenic, myogenic, and endothelial, pathways (data not shown). These are characteristic lineages generated from mesenchymal stem cells (MSC) obtained from bone marrow and other tissues (24), including amniotic fluid (25). However, unlike typical MSC, the AFS cells have been maintained in culture for over 100 population doublings with no evidence of senescence, karyotypic alteration, shortening of telomeres, or oncogenic transformation. Moreover, the AFS cells can give rise to non-mesenchymal cell types, including cells expressing markers of hepatocytes (7) or other endodermal derivatives.

The foregoing is illustrative of the present invention, and is not to be construed as limiting thereof. The invention is defined by the following claims, with equivalents of the claims to be included therein.

That which is claimed is:

1. A method of treating insulin-dependent diabetes in a human subject in need thereof, comprising the steps of:
   (i) providing a pharmaceutical composition comprising human amniotic fluid-derived stem cells, wherein said amniotic fluid-derived stem cells:
      (a) specifically bind c-kit antibodies at the time of collection,
      (b) are transfected with a nucleic acid expressing Pdx-1,
      (c) express the cell surface marker CD44 and do not express CD34 and CD105 cell surface markers, and
   (ii) administering the pharmaceutical composition of step (i) to said human subject in an amount effective to treat said insulin-dependent diabetes.

2. The method of claim 1, wherein said human amniotic fluid-derived stem cells:
   (a) proliferate through at least 200 population doublings when grown in vitro,
   (b) do not require feeder cell layers to grow in vitro, and
   (c) do not form teratomas when grown in vivo.

3. The method of claim 1, wherein said administering step is carried out by intraveneous or intraarterial injection.

4. The method of claim 1, wherein said cells are administered in an amount of from about $1 \times 10^5$ to about $1 \times 10^9$ cells per subject.

5. The method of claim 1, wherein said subject is effectively treated for said diabetes for at least two months after said administering step.

6. The method of claim 1, wherein said cells are not differentiated into pancreatic-like cells prior to said administering step.

7. The method of claim 1, wherein said cells are encapsulated in an insulin-permeable capsule.

8. The method of claim 1, wherein said cells are unencapsulated.

9. The method of claim 1, wherein said subject is an adult subject.

10. The method of claim 1, wherein said subject is an adolescent subject.

11. The method of claim 1, wherein said subject is a juvenile subject.

12. The method of claim 1, wherein said providing in step (i) is carried out by collecting amniotic fluid-derived stem cells from a human donor, and then expanding said human amniotic fluid-derived stem cells in vitro.

13. A pharmaceutical composition for the treatment of diabetes comprising amniotic fluid-derived stem cells, wherein said amniotic fluid-derived stem cells:
   (i) specifically bind c-kit antibodies at the time of collection,
   (ii) are transfected with a nucleic acid expressing Pdx-1,
   (iii) express the cell surface marker CD44 and do not express CD34 and CD105 cell surface markers, and
   (iv) are provided in a treatment-effective amount.

14. The composition of claim 13, wherein said composition comprises an aqueous carrier.

15. The composition of claim 13 in unit dosage form.

16. The composition of claim 13, wherein said composition is an injectable composition.

17. The composition of claim 13, wherein said amniotic fluid-derived stem cells are encapsulated in an insulin-permeable capsule.

18. The composition of claim 13, wherein said amniotic fluid-derived stem cells are unencapsulated.

19. The composition of claim 13, wherein said amniotic fluid-derived stem cells are human cells.

20. The composition of claim 13, wherein said amniotic fluid-derived stem cells:
   (i) are collected from amniotic fluid of a mammalian donor,
   (ii) differentiate upon appropriate stimulation into at least osteogenic, adipogenic, myogenic, neurogenic, hematopoietic, and endothelial cell lines,
   (iii) proliferate through at least 200 population doublings when grown in vitro,
   (iv) do not require feeder cell layers to grow in vitro, and
   (v) do not form teratomas when grown in vivo.

21. The composition of claim 13, wherein said amniotic fluid-derived stem cells express the transcription factor Oct-4, SSEA-1, Sca-1, and CD90.

22. The composition of claim 13, wherein said nucleic acid comprises DNA or RNA.

23. The composition of claim 13, wherein said nucleic acid is RNA.

24. The composition of claim 13, wherein said composition is isotonic with human blood.

25. The composition of claim 13, wherein said composition comprises from about $1 \times 10^5$ to about $1 \times 10^9$ of said cells.

26. The composition of claim 14, wherein said cells are provided as a suspension in the carrier.

27. A pharmaceutical composition for the treatment of diabetes comprising amniotic fluid-derived stem cells transfected with a nucleic acid expressing Pdx-1, wherein said amniotic fluid-derived stem cells:
   (i) are collected from amniotic fluid of a mammalian donor,
   (ii) proliferate through at least 200 population doublings when grown in vitro,
   (iii) do not require feeder cell layers to grow in vitro,
   (iv) do not form teratomas when grown in vivo,
   (v) specifically bind c-kit antibodies at the time of collection,
   (vi) express the cell surface marker CD44 and do not express CD34 and CD 105 cell surface markers, and
   (vii) are provided in a treatment-effective amount,
   wherein said composition is an injectable composition that is isotonic with human blood.

28. The composition of claim 27, wherein said amniotic fluid-derived stem cells are human cells.

29. The composition of claim 27, wherein said nucleic acid comprises DNA or RNA.

30. The composition of claim 27, wherein said nucleic acid is RNA.

31. The composition of claim 27, wherein said composition comprises from about $1 \times 10^5$ to about $1 \times 10^9$ of said cells.

32. The composition of claim 27, wherein said cells are provided as a suspension in a carrier.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial
<220> FEATURE:
<223> OTHER INFORMATION: PCR primer

<400> SEQUENCE: 1
```

```
cagtcacagc ggagtgaatc                                              20

<210> SEQ ID NO 2
<211> LENGTH: 19
<212> TYPE: DNA
<213> ORGANISM: Artificial
<220> FEATURE:
<223> OTHER INFORMATION: PCR primer

<400> SEQUENCE: 2
cgttcagctg aagtcgcat                                               19

<210> SEQ ID NO 3
<211> LENGTH: 20
<212> TYPE: DNA
<213> ORGANISM: Artificial
<220> FEATURE:
<223> OTHER INFORMATION: PCR primer

<400> SEQUENCE: 3
tggcactcag caaacagcga                                              20

<210> SEQ ID NO 4
<211> LENGTH: 20
<212> TYPE: DNA
<213> ORGANISM: Artificial
<220> FEATURE:
<223> OTHER INFORMATION: PCR primer

<400> SEQUENCE: 4
acccagagcc agacaggtct                                              20

<210> SEQ ID NO 5
<211> LENGTH: 20
<212> TYPE: DNA
<213> ORGANISM: Artificial
<220> FEATURE:
<223> OTHER INFORMATION: PCR primer

<400> SEQUENCE: 5
tgtaggcagt acgggtcctc                                              20

<210> SEQ ID NO 6
<211> LENGTH: 20
<212> TYPE: DNA
<213> ORGANISM: Artificial
<220> FEATURE:
<223> OTHER INFORMATION: PCR primer

<400> SEQUENCE: 6
ctcgaacatt tgaccccacc                                              20
```